(12) United States Patent
Lysenko et al.

(10) Patent No.: US 7,745,652 B2
(45) Date of Patent: Jun. 29, 2010

(54) INTEGRATED CHEMICAL PROCESSES FOR INDUSTRIAL UTILIZATION OF SEED OILS

(75) Inventors: Zenon Lysenko, Midland, MI (US); Bob R. Maughon, Midland, MI (US); Jozef Bicerano, Midland, MI (US); Kenneth A. Burdett, Midland, MI (US); Christopher P. Christenson, Lake Jackson, TX (US); Clark H. Cummins, Midland, MI (US); Marvin L. Dettloff, Lake Jackson, TX (US); Alan K. Schrock, Lake Jackson, TX (US); P. J. Thomas, Midland, MI (US); Richard D. Varjian, Saginaw, MI (US); Jerry E. White, Lake Jackson, TX (US); John Michael Maher, Charleston, WV (US)

(73) Assignee: Dow Global Technologies Inc., Midland, MI (US)

( * ) Notice: Subject to any disclaimer, the term of this patent is extended or adjusted under 35 U.S.C. 154(b) by 59 days.

(21) Appl. No.: 12/328,868

(22) Filed: Dec. 5, 2008

(65) Prior Publication Data

US 2009/0143544 A1    Jun. 4, 2009

Related U.S. Application Data

(63) Continuation of application No. 10/508,805, filed as application No. PCT/US03/11852 on Apr. 17, 2003, now Pat. No. 7,576,227.

(60) Provisional application No. 60/376,611, filed on Apr. 29, 2002.

(51) Int. Cl.
C07C 51/43    (2006.01)

(52) U.S. Cl. .............. 554/174; 585/639; 560/155; 560/179

(58) Field of Classification Search ............ 554/174; 560/155, 179; 585/639
See application file for complete search history.

(56) References Cited

OTHER PUBLICATIONS

Refvik et al., AOCS, vol. 76, pp. 93-98, 1999.*

* cited by examiner

Primary Examiner—Deborah D Carr

(57) ABSTRACT

Integrated processes of preparing industrial chemicals starting from seed oil feedstock compositions containing one or more unsaturated fatty acids or unsaturated fatty acid esters, which are essentially free of metathesis catalyst poisons, particularly hydroperoxides; metathesis of the feedstock composition with a lower olefin, such as ethylene, to form a reduced chain olefin, preferably, a reduced chain α-olefin, and a reduced chain unsaturated acid or ester, preferably, a reduced chain α,ω-unsaturated acid or ester. The reduced chain unsaturated acid or ester may be (trans)esterified to form a polyester polyolefin, which may be epoxidized to form a polyester polyepoxide. The reduced chain unsaturated acid or ester may be hydroformylated with reduction to produce an α,ω-hydroxy acid or α,ω-hydroxy ester, which may be (trans)esterified with a polyol to form an α,ω-polyester polyol. Alternatively, the reduced chain unsaturated acid or ester may be hydroformylated with reductive amination to produce an α,ω-amino acid or α,ω-amino ester, which may be (trans) esterified to form an α,ω-polyester polyamine.

25 Claims, No Drawings

US 7,745,652 B2

INTEGRATED CHEMICAL PROCESSES FOR INDUSTRIAL UTILIZATION OF SEED OILS

CROSS-REFERENCE TO RELATED APPLICATIONS

This application is a continuation application of U.S. application Ser. No. 10/508,805, filed Sep. 23, 2004, which is a 371 filing of International Patent Application PCT/US03/11852, filed Apr. 17, 2003, which claims the benefit of U.S. Provisional Application 60/376,611, filed Apr. 29, 2002.

BACKGROUND OF THE INVENTION

In one aspect, this invention pertains to an olefin metathesis feedstock composition and a metathesis process therefor. More specifically, this invention pertains to an unsaturated fatty acid or fatty acid ester feedstock composition and its metathesis with a lower olefin, primarily ethylene, in the presence of a metathesis catalyst to prepare a reduced chain olefin and a reduced chain unsaturated acid or ester, preferably a reduced chain $\alpha$-olefin and a reduced chain $\alpha,\omega$-unsaturated acid or ester.

In another aspect, this invention pertains to an integrated process involving first the metathesis of an unsaturated fatty acid or fatty acid ester feedstock composition with an olefin, preferably ethylene, to form a reduced chain unsaturated acid or ester, and thereafter, conversion of the reduced chain unsaturated acid or ester into an $\alpha,\omega$-hydroxy acid, $\alpha,\omega$-hydroxy ester, and/or an $\alpha,\omega$-diol. Alternatively, the reduced chain unsaturated acid or ester can be converted into an $\alpha,\omega$-amino acid, an $\alpha,\omega$-amino ester, and/or an $\alpha,\omega$-amino alcohol.

In yet another aspect, this invention pertains to an integrated process involving first the metathesis of an unsaturated fatty acid or fatty acid ester feedstock composition with an olefin, preferably ethylene, to form a reduced chain unsaturated acid or ester, and thereafter, conversion of the reduced chain unsaturated acid or ester into an epoxy acid or epoxy ester.

In other aspects, this invention pertains to polyester polyol, polyester polyamine, and polyester polyepoxide compositions.

Olefin (unsaturated) functionalities can be transformed into alcohol, amine, or epoxide functionalities via organic processes known in the art. In addition, monoacids and monoesters can be converted into polyesters via esterification or transesterification, respectively, with a polyol. Accordingly, unsaturated monoacids and monoesters have the potential to be converted into industrially useful polyester polyols, polyester polyamines, or polyester polyepoxides, preferably, $\alpha,\omega$-polyester polyols, $\alpha,\omega$-polyester polyamines, or $\alpha,\omega$-polyester polyepoxides. Polyols and polyamines find utility in the manufacture of urethane polymers. Polyepoxides find utility in the manufacture of epoxy resins. $\alpha$-Olefins, by themselves, find utility in the manufacture of polyolefin polymers.

In a search for non-petroleum-based, renewable sources of industrial chemicals, recent attention has turned to various seed oils, particularly those containing a high concentration of unsaturated fatty acid esters, such as the glycerides of oleic acid. Sunflower, canola, and certain soybean oils, for example, possess concentrations of oleic acid esters in excess of 70 weight percent. It is known, for example, to transesterify seed oil fatty acid esters with a lower alcohol, e.g., $C_{1-8}$ alcohol, such as methanol, to form unsaturated fatty acid esters of the lower alcohol. The latter can be metathesized with ethylene in the presence of a metathesis catalyst to form a reduced chain $\alpha$-olefin and a reduced-chain $\alpha,\omega$-unsaturated ester. As an example, methyl oleate can be metathesized with ethylene to prepare 1-decene and methyl-9-decenoate.

WO 96/04289 discloses a metathesis process wherein methyl oleate and ethylene are contacted in the presence of a metathesis catalyst comprising a ruthenium or osmium carbene compound, such as (dichloro-3,3-diphenylvinylcarbene)-ruthenium (II), to prepare 1-decene and methyl-9-decenoate. The patent discloses a catalyst turnover number (hereinafter "turnover number") of 143, when the process is run at room temperature and 100 psig (689 kPa) ethylene. For the purposes of this invention, the term "turnover number" shall be defined as the number of moles of unsaturated acid or ester that is metathesized, e.g., methyl oleate metathesized, per mole of catalyst.

Likewise, D. Mandelli et al. discloses in *Journal of the American Oil Chemical Society*, 73, no. 2 (1996), 229-232, the ethenolysis of esters of vegetable oils, e.g., methyl oleate with ethylene, over rhenium catalysts, and report a turnover number of 112. The methyl oleate is treated over alumina prior to use.

Disadvantageously, the aforementioned turnover numbers are too low to allow for commercial implementation of these metathesis processes.

M. D. Refyik et al. discloses in *Journal of the American Oil Chemical Society*, 76, no. 1 (1999), 93-98, that vegetable oils can be self-metathesized in the presence of Grubb's ruthenium catalyst, bis(tricyclohexylphosphine)benzylidine-ruthenium dichloride. The oils are taught to be purified over silica gel prior to use. Additional art disclosing the self-metathesis of unsaturated fatty acid esters includes purification of the unsaturated esters over silica or alumina prior to use, as reported, for example, by W. Buchowicz et al. in *Journal of Molecular Catalysis A: Chemical* 148 (1999), 97-103, and by P. O, Nubel et al. in *Journal of Molecular Catalysis A: Chemical*, 145 (1999), 323-327. A turnover number of between 650 and 2,500 is reported for methyl oleate. Disadvantageously, the metathesis of unsaturated fatty acid esters with ethylene is more problematical than the self-metathesis of unsaturated fatty acid esters. Accordingly, a significantly lower turnover number is expected when ethylene or other olefin of low molecular weight is used as a co-reactant.

C. Demes discloses in *Chemosphere*, 43 (2001), 39, the metathesis of methyl oleate with ethylene in the presence of a ruthenium metathesis catalyst. The process is taught to exhibit total catalyst turnover numbers of between 2,320 and 2,960 at 50° C. and 145 psi.

The implementation of integrated chemical processes derived from renewable, seed-oil feedstocks may depend significantly upon the productivity of the metathesis stage, wherein an unsaturated fatty acid or unsaturated fatty acid ester feedstock derived from seed oils is metathesized with a lower olefin, such as ethylene. Productivity can be measured, for example, by catalyst activity (e.g., conversion of unsaturated fatty acid or ester) and turnover number. Disadvantageously, prior art metathesis processes exhibit unacceptable productivity. Unless unsaturated fatty acids and esters derived from seed oils can be converted into reduced chain olefins and reduced chain unsaturated acids or esters in higher productivity, as compared with prior art processes, the integration of the metathesis process with other downstream industrially useful processes may be difficult to achieve commercially.

In view of the above, a need exists for discovery of an improved process wherein an unsaturated fatty acid or fatty acid ester feedstock composition, derived from a seed oil, is metathesized with a lower olefin, such as ethylene, to produce a reduced chain olefin and a reduced chain unsaturated acid or ester in acceptable productivity. Such a process would require a catalyst of higher activity and turnover number, as compared with prior art catalysts. Moreover, any improved process should achieve these improved results under acceptable process conditions (particularly, mild temperature and pressure and minimal diluent or solvent) and at acceptable selectivity to the desired metathesis products. A metathesis process having the aforementioned properties might beneficially be applied to converting unsaturated fatty acids and fatty acid esters derived from renewable seed oils into reduced chain olefins and reduced chain unsaturated acids and esters, preferably, reduced chain α-olefins and reduced chain α,ω-unsaturated acids and esters. Reduced chain olefins of these types could be integrated into downstream processes for preparing useful industrial chemicals, such as, polyester polyols, polyester polyamines, polyester polyepoxides, and poly(olefins).

SUMMARY OF THE INVENTION

In a first aspect, this invention provides for a novel olefin metathesis process of converting two reactant olefins, one of which is derived from a seed oil, into two product olefins that are different from the reactant olefins. The novel metathesis process comprises contacting a fatty acid or fatty acid ester feedstock composition comprising one or more unsaturated fatty acids or unsaturated fatty acid esters, as the case may be, with a lower olefin in the presence of a metathesis catalyst under metathesis process conditions sufficient to prepare a reduced chain olefin and a reduced chain unsaturated acid or ester, respectively. In an important aspect of this invention, the fatty acid or fatty acid ester feedstock composition is characterized as being essentially free of poison(s) capable of inhibiting the metathesis catalyst, as described hereinafter. These poisons are found inherent in the raw material feedstocks used for this metathesis and are formed as a consequence of normal exposure to atmospheric conditions. For the purposes of this invention, the term "reduced chain" shall mean that the chain length of a product olefin so described is shorter than the chain length of the reactant olefin from which the product olefin is derived.

In a related aspect, this invention provides for a novel fatty acid or fatty acid ester composition derived from a seed oil and comprising one or more unsaturated fatty acids or unsaturated fatty acid esters, characterized as comprising less than 3.0 milliequivalents metathesis catalyst poison(s) per kilogram of fatty acid or fatty acid ester composition.

Advantageously, the metathesis process of this invention employs a fatty acid or fatty acid ester feedstock composition derived from a seed oil, more advantageously, a fatty acid or fatty acid ester feedstock composition derived from a seed oil and of purified form so as to deliver improved operability to the metathesis catalyst. Even more advantageously, the metathesis process of this invention exhibits improved productivity, as compared with prior art metathesis processes. Beneficially, the metathesis process of this invention in preferred embodiments achieves higher olefin conversion and higher turnover numbers, as compared with prior art processes. Moreover, these improvements are achieved under mild process conditions of temperature and pressure and with minimal diluent or solvent, if any. The aforementioned improved properties render the metathesis process of this invention highly desirable for converting unsaturated fatty acids and unsaturated fatty acid esters derived from seed oils into higher value products, including, reduced chain olefins and reduced chain unsaturated acids and esters.

The aforementioned novel metathesis process of this invention allows for the beneficial exploitation of seed oils as a renewable source of non-petroleum-based industrial chemicals via integration of the metathesis process with downstream chemical processes. For example, the novel metathesis process of this invention finds utility in the preparation of reduced chain olefins, preferably α-olefins, and reduced chain unsaturated acids and esters, preferably α,ω-unsaturated acids and esters. α-Olefins are valuable starting monomers in the preparation of polyolefin polymers. α,ω-Unsaturated acids and esters can be converted via a combination of (trans)esterification and other known chemistries, such as epoxidation or hydroformylation with reduction or reductive amination, into polyester polyepoxides, polyester polyols, diols, polyester polyamines, and amino alcohols. Polyester polyepoxides are useful in the manufacture of epoxy thermoset resins. Polyester polyols, diols, polyester polyamines, and amino alcohols find utility in the manufacture of polyurethanes.

In a second aspect, this invention provides for a novel process of preparing a polyester polyepoxide. In this second aspect, the process comprises (1) contacting a fatty acid or fatty acid ester feedstock composition comprising one or more unsaturated fatty acids or unsaturated fatty acid esters with a lower olefin in the presence of an olefin metathesis catalyst under metathesis process conditions sufficient to prepare a reduced chain unsaturated acid or ester; the fatty acid or fatty acid ester feedstock composition being characterized as being essentially free of poison(s) capable of inhibiting the metathesis catalyst; (2) (trans)esterifying the reduced chain unsaturated acid or ester with a polyol under (trans)esterification conditions sufficient to prepare an unsaturated polyester; and (3) epoxidizing the unsaturated polyester with an epoxidizing agent, optionally in the presence of an epoxidation catalyst, under epoxidation conditions sufficient to prepare a polyester polyepoxide.

In connection with the above-described metathesis-(trans) esterification process, this invention also provides for a novel polyester polyolefin composition represented by formula (I) hereinbelow:

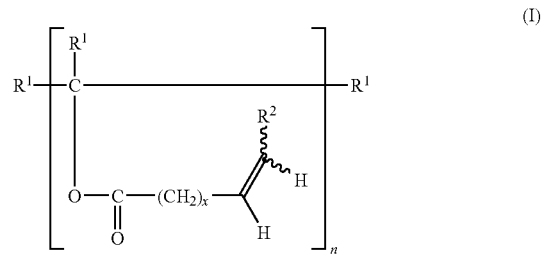

wherein each $R^1$ is independently selected from hydrogen and $C_{1-8}$ alkyl radicals; $R^2$ is selected from hydrogen, methyl, ethyl, and vinyl radicals; x is an integer from about 3 to about 7; and n is an integer from 2 to about 15.

In connection with the above-described metathesis-(trans) esterification-epoxidation process, this invention also provides for a novel polyester polyepoxide composition represented by formula (II) hereinbelow:

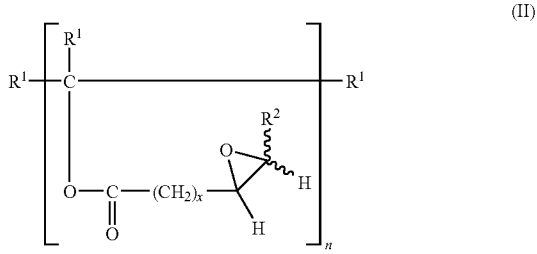

(II)

wherein each $R^1$ is independently selected from hydrogen and $C_{1-8}$ alkyl radicals; $R^2$ is selected from hydrogen, methyl, ethyl, and vinyl radicals; x is an integer from about 3 to about 7; and n is an integer from 2 to about 15.

In a third aspect, this invention provides for a process of preparing a reduced chain α,ω-hydroxy acid, α,ω-hydroxy ester, and/or α,ω-diol. In this third aspect, the process comprises (1) contacting a fatty acid or fatty acid ester feedstock composition comprising one or more unsaturated fatty acids or fatty acid esters with a lower olefin in the presence of an olefin metathesis catalyst under process conditions sufficient to prepare a reduced chain unsaturated acid or ester, as the case may be; the fatty acid or fatty acid ester feedstock composition characterized as being essentially free of poison(s) capable of inhibiting the metathesis catalyst; and (2) subjecting the reduced chain unsaturated acid or ester to hydroformylation with reduction in the presence of a hydroformylation/reduction catalyst under hydroformylation/reduction conditions sufficient to produce an α,ω-hydroxy acid, α,ω-hydroxy ester, and/or α,ω-diol. Optionally, in a third process step (3), the α,ω-hydroxy acid, hydroxy ester, and/or diol may be (trans)esterified under (trans)esterification conditions sufficient to prepare an α,ω-polyester polyol.

In connection with the above-described metathesis-hydroformylation-(trans)esterification process invention, this invention provides for a novel α,ω-polyester polyol composition represented by formula (III) hereinbelow:

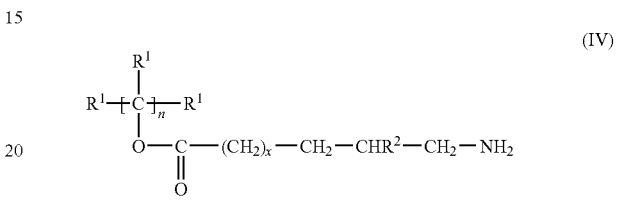

(III)

wherein each $R^1$ is independently selected from hydrogen and $C_{1-8}$ alkyl radicals; $R^2$ is selected from hydrogen, methyl, ethyl, and vinyl radicals; x is an integer from about 3 to about 7; and n is an integer from 2 to about 15.

In a fourth aspect, this invention provides for a process of preparing a reduced chain α,ω-amino acid, α,ω-amino ester, and/or α,ω-amino alcohol. In this fourth aspect, the process comprises (1) contacting a fatty acid or fatty acid ester feedstock composition comprising one or more unsaturated fatty acids or fatty acid esters, as the case may be, with a lower olefin in the presence of an olefin metathesis catalyst under process conditions sufficient to prepare a reduced chain unsaturated acid or ester; the fatty acid or fatty acid ester feedstock composition being characterized as being essentially free of poison(s) capable of inhibiting the metathesis catalyst; and thereafter (2) subjecting the reduced chain unsaturated acid or ester to hydroformylation with reductive amination in the presence of a hydroformylation catalyst under hydroformylation/-reductive amination conditions sufficient to produce an α,ω-amino acid, α,ω-amino ester, and/ or α,ω-amino alcohol. Optionally, in a third process step (3), the α,ω-amino acid, amino ester, and/or amino alcohol may be (trans)esterified under (trans)esterification conditions sufficient to prepare an α,ω-polyester polyamine.

In connection with the above-described metathesis-hydroformylation-reductive amination-(trans)esterification process invention, this invention also provides for a novel α,ω-polyester polyamine composition represented by formula (IV) hereinbelow:

$$R^1 + C +_n R^1 \atop O—C—(CH_2)_x—CH_2—CHR^2—CH_2—NH_2 \atop \| \atop O$$

(IV)

wherein each $R^1$ is independently selected from hydrogen and $C_{1-8}$ alkyl radicals; $R^2$ is selected from hydrogen, methyl, ethyl, and vinyl radicals; x is an integer from 3 to about 7; and n is an integer from 2 to about 15.

DETAILED SUMMARY OF THE INVENTION

As described hereinabove, novel integrated processes are provided related to the preparation of novel polyester polyepoxides, α,ω-polyester polyols, and α,ω-polyester polyamines, starting from a purified unsaturated fatty acid or fatty acid ester feedstock composition derived from renewable seed oil feedstocks.

In a first aspect, a novel olefin metathesis process is disclosed for converting two reactant olefins, one of which is derived from a seed oil, into two product olefins, preferably, α-olefins, that are different from the reactant olefins. The novel metathesis process comprises contacting a fatty acid or fatty acid ester feedstock composition comprising one or more unsaturated fatty acids or unsaturated fatty acid esters, preferably oleic acid esters, with a lower olefin, preferably ethylene, in the presence of an olefin metathesis catalyst under metathesis process conditions sufficient to prepare a reduced chain olefin, and a reduced chain unsaturated acid or ester. Preferably, the products include a reduced chain α-olefin and a reduced chain α,ω-unsaturated acid or ester. The term "reduced chain" shall mean that the chain length of the product olefin so described is shorter than the chain length of the reactant olefin from which the product olefin is derived. In an important aspect of this invention, the feedstock composition is provided to the metathesis process in a form that is essentially free of poison(s) capable of inhibiting the metathesis catalyst, most notably, organic hydroperoxide poisons. For the purposes of this invention, the phrase "essentially free of poison(s) capable of inhibiting the metathesis catalyst" shall be taken to mean that the fatty acid or fatty acid ester feedstock composition comprises less than about 100 milliequivalents of metathesis poison(s), preferably, organic hydroperoxides, per kilogram of feedstock composition (meq/kg). By reducing the poison(s) in the feedstock composition to a level below 100 meq/kg, and to preferred lower levels as noted hereinafter, the metathesis process achieves improved productivity, which renders the process more adaptable to commercial use.

In a preferred embodiment of this invention, the fatty acid feedstock composition comprises greater than about 70 weight percent oleic acid. In another preferred embodiment, the fatty acid ester feedstock composition comprises greater than about 70 weight percent methyl oleate.

In yet another preferred embodiment of this invention, the reduced chain olefin is an α-olefin, more preferably, 1-decene. In a further preferred aspect of this invention, the reduced chain unsaturated acid or ester is an α,ω-unsaturated acid or ester; more preferably, decenoic acid or methyl 9-decenoate.

In a related aspect, this invention provides for a novel fatty acid or fatty acid ester feedstock composition comprising one or more unsaturated fatty acids or fatty acid esters (as the case may be), further characterized as comprising less than 3.0 meq metathesis catalyst poison(s) per kg of fatty acid or fatty acid ester composition. Preferably, the fatty acid or fatty acid ester feedstock composition comprises less than about 2.5, even more preferably, less than about 2.0, yet more preferably, less than about 1.5, and most preferably, less than about 1.0 meq metathesis catalyst poison(s)/kg feedstock.

In a second aspect, this invention provides for a novel process of preparing a polyester polyepoxide, preferably, an α,ω-polyester polyepoxide. In this second aspect, the process comprises (1) contacting a fatty acid or fatty acid ester feedstock composition comprising one or more unsaturated fatty acids or unsaturated fatty acid esters, preferably oleic acid or oleic acid esters, with a lower olefin, preferably ethylene, in the presence of an olefin metathesis catalyst under metathesis conditions sufficient to prepare a reduced chain unsaturated acid or ester; the feedstock composition being characterized as being essentially free of poison(s) capable of inhibiting the metathesis catalyst; (2) subjecting the reduced chain unsaturated acid or ester to (trans)esterification with a polyol under (trans)esterification conditions sufficient to prepare an polyester polyolefin; and (3) epoxidizing the polyester polyolefin with an epoxidizing agent, optionally, in the presence of an epoxidation catalyst, under epoxidation conditions sufficient to prepare a polyester polyepoxide. Preferably, the reduced chain unsaturated acid or ester is a reduced chain α,ω-unsaturated acid or ester. Preferably, the polyester polyolefin is an α,ω-polyester polyolefin; and preferably, the polyester polyepoxide is an α,ω-polyester polyepoxide.

In connection with the above-described metathesis-(trans) esterification process, this invention provides for a novel polyester polyolefin composition represented by formula (I) hereinbelow:

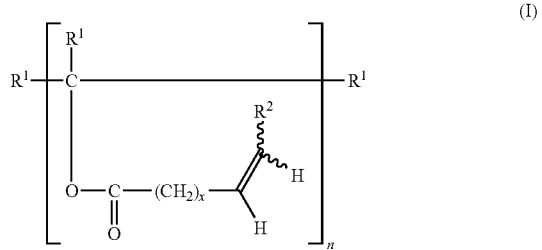

wherein each $R^1$ is independently selected from hydrogen and $C_{1-8}$ alkyl radicals, preferably, hydrogen; $R^2$ is selected from hydrogen, methyl, ethyl, and vinyl radicals, preferably, hydrogen; x is an integer from about 3 to about 7, preferably, about 7; and n is an integer from 2 to about 15, preferably, about 3.

In connection with the above-described metathesis-(trans) esterification-epoxidation process, this invention also provides for a novel polyester polyepoxide composition represented by formula (II) hereinbelow:

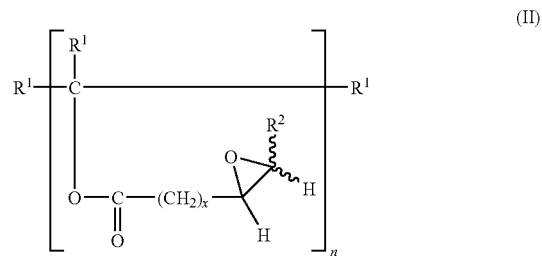

wherein each $R^1$ is independently selected from hydrogen and $C_{1-8}$ alkyl radicals, preferably, hydrogen; $R^2$ is selected from hydrogen, methyl, ethyl, and vinyl radicals, preferably, hydrogen; x is an integer from about 3 to about 7, preferably, about 7; and n is an integer from 2 to about 15, preferably, about 3. Most preferably, each $R^1$ and $R^2$ is hydrogen; x is 7; n is 3; and the polyester polyepoxide is the triglyceride of 9,10-epoxydecanoic acid.

In a third aspect, this invention provides for a process of preparing an α,ω-hydroxy acid, α,ω-hydroxy ester, and/or α,ω-diol. In this third aspect, the process comprises (1) contacting a fatty acid or fatty acid ester feedstock composition comprising one or more unsaturated fatty acids or fatty acid esters, preferably oleic acid or oleic acid esters, with a lower olefin, preferably ethylene, in the presence of an olefin metathesis catalyst under process conditions sufficient to prepare a reduced chain unsaturated acid or ester; the feedstock composition being characterized as being essentially free of poison(s) capable of inhibiting the metathesis catalyst; and (2) subjecting the reduced chain unsaturated acid or ester to hydroformylation with reduction in the presence of a hydroformylation/reduction catalyst under hydroformylation/reduction process conditions sufficient to produce an (α,ω-hydroxy acid, α,ω-hydroxy ester, and/or α,ω-diol. Preferably, the reduced chain unsaturated acid or ester is a reduced chain α,ω-unsaturated acid or ester. In more preferred embodiments of this invention, the α,ω-hydroxy ester is methyl 11-hydroxy-undecanoate; the α,ω-hydroxy acid is 11-hydroxy-undecanoic acid; and the α,ω-diol is 1,11-dihydroxyundecane. Optionally, in a third step (3), the α,ω-hydroxy acid, ester, and/or diol may be subjected to (trans) esterification under (trans)esterification conditions sufficient to produce a polyester polyol, preferably, an α,ω-polyester polyol.

The α,ω-polyester polyol produced in the aforementioned metathesis-hydroformylation-(trans)esterification process may be represented by formula (III) hereinbelow:

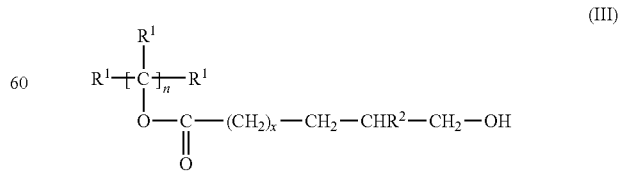

wherein each $R^1$ is independently selected from hydrogen and $C_{1-8}$ alkyl radicals, preferably, hydrogen; $R^2$ is selected from hydrogen, methyl, ethyl, and vinyl radicals, preferably, hydrogen; x is an integer from about 3 to about 7, preferably, about 7; and n is an integer from 2 to about 15, preferably, about 3. Thus, in the most preferred embodiment, each $R^1$ and $R^2$ is hydrogen; x is 7; n is 3; and the polyester polyol is the triglyceride ester of 11-hydroxyundecanoic acid.

In a fourth aspect, a process is disclosed herein of preparing an α,ω-amino acid, α,ω-amino ester, and/or α,ω-amino alcohol. In this fourth aspect, the process comprises (1) contacting a fatty acid or fatty acid ester feedstock composition comprising one or more unsaturated fatty acids or fatty acid esters, preferably oleic acid or oleic acid esters, with a lower olefin, preferably ethylene, in the presence of an olefin metathesis catalyst under process conditions sufficient to prepare a reduced chain unsaturated acid or ester; the feedstock composition being characterized as being essentially free of poison(s) capable of inhibiting the metathesis catalyst; and thereafter (2) subjecting the reduced chain unsaturated acid or ester to hydroformylation with reductive amination in the presence of a hydroformylation/reduction catalyst under hydroformylation/reductive amination conditions sufficient to produce an α,ω-amino acid, α,ω-amino ester, and/or α,ω-amino alcohol. In a preferred embodiment, the reduced chain unsaturated acid or ester is a reduced chain α,ω-unsaturated acid or ester. In a preferred embodiment, the α,ω-amino ester is methyl 11-aminoundecanoate. Likewise, the preferred α,ω-amino acid is 11-aminoundecanoic acid, and the preferred α,ω-amino alcohol is 11-aminoundecanol. Optionally, in a third process step (3), the α,ω-amino acid, amino ester, and/or amino alcohol may be (trans)esterified under (trans) esterification conditions sufficient to prepare an α,ω-polyester polyamine.

In connection with the above-described metathesis-hydroformylation-amination-(trans)esterification process invention, this invention also provides for a novel α,ω-polyester polyamine composition represented by formula (IV) hereinbelow:

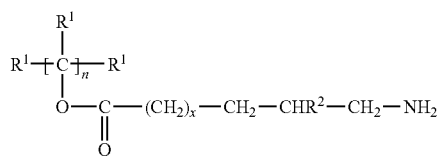

(IV)

wherein each $R^1$ is independently selected from hydrogen and $C_{1-8}$ alkyl radicals, preferably, hydrogen; $R^2$ is independently selected from hydrogen, methyl, ethyl, and vinyl radicals, preferably, hydrogen; x is an integer from about 3 to about 7, preferably, about 7; and n is an integer from 2 to about 15, preferably, about 3. Thus, in a most preferred embodiment, the polyester polyamine is an α,ω-polyester polyamine. Most preferably, each $R^1$ and $R^2$ is hydrogen; x is 7; n is 3; and the polyester polyamine is the triglyceride of 11-aminoundecanoic acid.

In a most preferred embodiment, this invention provides for a novel olefin metathesis process comprising contacting ethylene with a fatty acid ester feedstock composition that is derived from a seed oil and that comprises greater than about 80 weight percent methyl oleate, the fatty acid ester feedstock composition containing less than about 100 meq organic hydroperoxides per kg feedstock, in the presence of a metathesis catalyst under metathesis process conditions sufficient to prepare 1-decene and methyl-9-decenoate.

In another most preferred embodiment, this invention provides for a novel process of preparing an α,ω-polyester polyepoxide comprising the triglyceride ester of 9,10-epoxydecanoic acid. The most preferred process in this regard comprises (1) contacting ethylene with a fatty acid ester feedstock composition, which is derived from a seed oil and which comprises greater than about 80 weight percent methyl oleate, and which further comprises less than about 100 meq organic hydroperoxides per kg of fatty acid ester feedstock composition, in the presence of an olefin metathesis catalyst under metathesis process conditions sufficient to prepare methyl 9-decenoate; (2) transesterifying the methyl 9-decenoate with glycerol under transesterification conditions sufficient to prepare the triglyceride ester of 9-decenoic acid; and (3) epoxidizing the triglyceride ester of 9-decenoic with an epoxidizing agent, optionally, in the presence of an epoxidation catalyst, under epoxidation conditions sufficient to prepare the triglyceride ester of 9,10-epoxydecanoic acid.

In a third most preferred aspect, this invention provides for a process of preparing an α,ω-hydroxy ester or α,ω-diol comprising methyl 11-hydroxyundecanoate or 1,11-undecanediol (1,11-dihydroxyundecane), respectively. In this third most preferred aspect, the process comprises (1) contacting ethylene with a fatty acid ester feedstock composition that is derived from a seed oil and that comprises greater than about 80 weight percent methyl oleate, and that further comprises less than about 100 meq organic hydroperoxides per kg fatty acid ester composition, in the presence of an olefin metathesis catalyst under process conditions sufficient to prepare methyl-9-decenoate; and (2) subjecting the methyl-9-decenoate to hydroformylation with reduction in the presence of a rhodium hydroformylation catalyst and a reduction catalyst under hydroformylation/reduction conditions sufficient to produce methyl 11-hydroxyundecanoate and/or 1,11-undecanediol. Optionally, in a third process step (3), methyl 11-hydroxyundecanoate is transesterified by contact with glycerol under transesterification conditions sufficient to prepare the triglyceride ester of 11-hydroxyundecananoic acid.

In a fourth most preferred aspect, this invention provides for a process of preparing a reduced chain α,ω-amino ester, most preferably methyl-1-aminoundecanoate. In this fourth most preferred aspect, the process comprises (1) contacting ethylene with a fatty acid ester feedstock composition that is derived from a seed oil and that comprises greater than about 80 weight percent methyl oleate, and that further comprises less than about 100 meq of organic hydroperoxides per kg of fatty acid ester composition, in the presence of a metathesis catalyst under process conditions sufficient to prepare methyl-9-decenoate; and thereafter (2) subjecting the methyl-9-decenoate to hydroformylation with reductive amination in the presence of a hydroformylation catalyst under hydroformylation/reductive amination conditions sufficient to produce methyl-11-aminoundecanoate. Optionally, in a third process step (3), the methyl-11-aminoundecanoate is transesterified by contact with glycerol under transesterification conditions sufficient to prepare the triglyceride ester of 11-aminoundecanoic acid.

The fatty acid and fatty acid ester feedstock compositions suitable for use in the process of this invention comprise a substantial concentration of unsaturated fatty acid(s), unsaturated fatty acid ester(s), or mixture thereof. Typically, the feedstock composition for use in this process will comprise greater than about 60 weight percent unsaturated fatty acid(s) and/or unsaturated fatty acid ester(s), more preferably, greater than about 70 weight percent, and even more preferably, greater than about 80 weight percent, unsaturated fatty acid(s) and/or unsaturated fatty acid ester(s). Feedstock compositions meeting these criteria can be derived from plant and vegetable oils, including castor, olive, peanut, rapeseed, corn, sesame, cottonseed, soybean, sunflower, canola, safflower, linseed, and like oils. Preferably, the feedstock composition is derived from sunflower, canola, and certain genetically modified oils, including genetically modified soybean oils.

Generally, the fatty acid ester feedstock composition employed in this invention may be obtained by transesterifying a seed oil with a lower alkanol. In this context, the lower alkanol is typically taken as a $C_{1-10}$ alkanol, preferably, a $C_{1-8}$ alkanol, more preferably, a $C_{1-4}$ alkanol, such as, methanol, ethanol, isopropanol, or butanol, and most preferably, methanol. Seed oils comprise mixtures of both saturated and unsaturated fatty acid glycerides. Transesterification of the seed oil with a lower alkanol produces the corresponding mixture of saturated and unsaturated fatty acid esters of the lower alkanol. Because mixtures of glycerides can be difficult to process and separate, transesterification of the seed oil with a lower alkanol produces a fatty acid ester mixture that is more suitable for chemical transformations and separation. Any transesterification conditions are suitable, so long as the ester products of the lower alkanol are achieved. The art adequately discloses the transesterification (e.g., methanolysis, ethanolysis) of seed oils; for example, see WO 2001/012581, DE 19908978, BR 953081, incorporated herein by reference.

As a general transesterification method, a lower alcohol, preferably a $C_{1-10}$ alkanol, such as, methanol or ethanol, is contacted with alkali metal, preferably sodium, at a temperature between about 30° C. and about 100° C. to prepare the corresponding metal alkoxide. Afterwards, the seed oil is added, and the resulting reaction mixture is heated further at a temperature between about 30° C. and about 100° C. until transesterification is effected. The crude transesterified composition can be isolated by methods known in the art, including, for example, phase separation, extraction and distillation methods. The crude product can be decolorized over charcoal and separated from other or undesirable co-products by column chromatography, for example, over silica gel. Variations on the above general procedure are well documented in the art.

If rather than a fatty acid ester feedstock, a fatty acid feedstock is desirably employed, then the selected seed oil can be hydrolyzed to obtain the corresponding mixture of fatty acids. Methods for hydrolyzing seed oils to their constituent fatty acids are also well-documented in the art.

For the metathesis process, any fatty acid or fatty acid ester feedstock composition can be suitably employed, provided that the unsaturated fatty acids or unsaturated fatty acid esters contained therein can be metathesized to form reduced chain olefins and reduced chain unsaturated acids or esters. As known in the art, an unsaturated fatty acid ester is the ester condensation product of an unsaturated fatty acid and an alcohol. The unsaturated fatty acid comprises an extended carbon chain containing at least one carbon-carbon double bond and terminating in a carboxylic acid group. Typically, the unsaturated fatty acid will contain greater than about 6 carbon atoms, preferably, greater than about 10 carbon atoms, and more preferably, greater than about 12 carbon atoms. Typically, the unsaturated fatty acid will contain less than about 50 carbon atoms, preferably, less than about 36 carbon atoms, and more preferably, less than about 26 carbon atoms. At least one carbon-carbon double bond is present along the carbon chain, this double bond usually occurring about the middle of the chain, but not necessarily at this position. Unsaturated fatty acids containing two or more carbon-carbon double bonds may also be suitably employed in the process of this invention. Since metathesis can occur at any of the carbon-carbon double bonds, a fatty acid having more than one double bond may produce a variety of metathesis products that may then require more extensive separation efforts. Accordingly, unsaturated fatty acids containing one carbon-carbon double bond are preferred. The unsaturated fatty acid may be straight chain or branched and substituted along the fatty acid chain with one or more substituents, provided that the one or more substituents are substantially inert with respect to the metathesis process. Non-limiting examples of suitable substituents include alkyl moieties, preferably $C_{1-10}$ alkyl moieties, including for example methyl, ethyl, propyl, butyl, and the like; cycloalkyl moieties, preferably, $C_{4-8}$ cycloalkyl moieties, including for example, cyclopentyl and cyclohexyl; monocyclic aromatic moieties, preferably, $C_6$ aromatic moieties, that is, phenyl; arylalkyl moieties, preferably, $C_{7-16}$ arylalkyl moieties, including, for example, benzyl; and alkylaryl moieties, preferably, $C_{7-16}$ alkylaryl moieties, including, for example, tolyl, ethylphenyl, xylyl, and the like; as well as hydroxyl, ether, keto, aldehyde, and halide, preferably, chloro and bromo, functionalities.

Non-limiting examples of unsaturated fatty acids that may be suitably employed in the fatty acid feedstock or the fatty acid segment of the ester feedstock include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (godoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), cis-5-docosenoic, cis-5,13-docosadienoic and like acids. The most preferred unsaturated fatty acid is oleic acid, which contains a chain of eighteen carbon atoms with one double bond at the 9-carbon position.

The alcohol segment of the fatty acid esters present in the feedstock composition can be any monohydric, dihydric, or polyhydric alcohol capable of condensation with the unsaturated fatty acid to form the ester. In seed oils the alcohol segment is glycerol, a trihydric alcohol. By way of transesterification, the glycerides can be converted to fatty acid esters of lower alkanols, which are more readily separated or suitable for downstream chemical processing. Typically, the alcohol contains at least one carbon atom. Typically, the alcohol contains less than about 15 carbon atoms, preferably, less than about 12 carbon atoms, more preferably, less than about 10 carbon atoms, and even more preferably, less than about 8 carbon atoms. The carbon atoms in the alcohol segment may be arranged in a straight-chain or branched structure, and may be substituted with a variety of substituents, such as those previously disclosed hereinabove in connection with the fatty acid segment, including the aforementioned alkyl, cycloalkyl, monocyclic aromatic, arylalkyl, alkylaryl, hydroxyl, halogen, ether, ester, aldehyde and keto substituents. Preferably, the alcohol is a straight-chain or branched $C_{1-8}$ alkanol. Most preferably, the alcohol is a $C_{1-4}$ alkanol, suitable examples of which include methanol, ethanol, propanols, and butanols. Most preferably, the fatty acid ester feedstock composition comprises a mixture of the methyl esters of unsaturated fatty acids, predominantly, oleic acid.

As a condition of this invention, the fatty acid or fatty acid ester feedstock composition, typically derived via hydrolysis or transesterification of the seed oil, is of purified form, that is, essentially free of one or more poisons that inhibit the performance of the metathesis catalyst. Inhibition by poisoning is expressed by reduced catalyst activity, including reduced turnover number and reduced catalyst lifetime, as compared with a catalyst operating in an essentially poison-free environment. Typical poisons include organic hydroperoxides and peroxide decomposition products, such as water, alcohols, (e.g., allylic alcohols), ketones, and aldehydes (e.g., dienals). Compounds present in the feed, but not necessarily derived from hydroperoxides may also function as poisons, including, water, alcohols, (e.g., allylic alcohols), ketones, and aldehydes (e.g., dienals). The organic hydroperoxides are believed to be more ubiquitous and damaging. It is generally known that organic hydroperoxides may arise through the free radical air oxidation at the double bonds present in the unsaturated fatty acid. By purifying the feedstock to remove the poisons, preferably, organic hydroperoxide poisons, the metathesis catalyst can achieve a significantly improved activity, as measured by turnover number.

Seed oils, either unmodified or modified by hydrolysis or transesterification, may be purchased with acceptable purity, or alternatively, may be purified to a higher level of purity by the procedure described hereinafter. The purity of commercial fatty acid or fatty acid ester feedstocks generally varies from sample to sample; therefore such feedstocks are preferably subjected to purification for the purpose of achieving consistently low levels of catalyst poisons. If a sample is to be purified, then purification just prior to use in the metathesis process is preferred; however, storage of the purified feedstock under an inert atmosphere, such as nitrogen, may be acceptable for a period of time. The purification process itself is readily accomplished by contacting the fatty acid or fatty acid ester feedstock composition with an adsorbent that functions to remove the catalyst poison(s) to the low concentrations specified herein. Typical adsorbents include aluminas, silicas, activated carbons, clays, magnesias, aluminosilicates, molecular sieves, titanosilicates, and mixtures thereof. More preferred adsorbents include aluminas, clays, and aluminosilicates; even more preferred are clays and activated aluminas. The most preferred adsorbent is activated alumina.

More specifically, the purification process comprises contacting the fatty acid or fatty acid ester feedstock composition with the adsorbent under conditions sufficient to produce a purified feedstock composition having a total concentration of catalyst poison(s), preferably, organic hydroperoxides, of less than about 100 milliequivalents per kilogram (meq/kg) feedstock. Preferably, the total concentration of catalyst poison(s), preferably, organic hydroperoxides, is less than about 25, more preferably, less than about 15, even more preferably, less than about 10, and most preferably, less than 3.0 meq poison(s)/kg feedstock. Within the most preferred range of less than 3.0 meq/kg, it is preferred to employ a fatty acid or fatty acid ester feedstock composition comprising less than about 2.5, even more preferably, less than about 2.0, yet more preferably, less than about 1.5, and most preferably, less than about 1.0 meq poison(s)/kg feedstock. Methods of analyzing for hydroperoxides are well known in the art, as described, for example, by R. M. Johnson and I. W. Siddiqi in *The Determination of Organic Peroxides*, Pergamon Press, New York, N.Y., 1970, and as described in the American Oil Chemical Society Official Methods Cd 8-53 and Cd 8b-90; relevant sections of the aforementioned citations being incorporated herein by reference. Generally, different metathesis catalysts exhibit different degrees of sensitivity to metathesis poisons. For a metathesis process to be suitable for practical adaptation, it has now been discovered that the maximum concentration of poison(s) in the metathesis feedstock beneficially comprises less than about 100 meq/kg.

The adsorbent may be slurried with the crude feedstock composition, or preferably, provided in a fixed bed column through which the crude feedstock composition is passed. Typically, the amount of adsorbent used is greater than about 1 weight percent and less than about 100 weight percent, relative to the weight of the feedstock composition. Any temperature at which the feedstock composition is chemically and thermally stable and has a viscosity suitable for flowing through the adsorbent may be employed. The temperature is typically greater than about 10° C., and preferably, equal to or greater than about ambient, taken as 21° C. Typically, the temperature is less than about 100° C., preferably, less than about 50° C. The external pressure applied to the adsorbent column may generally range from atmospheric up to about 100 psig (690 kPa). Multiple passes through the adsorbent column or multiple contacts with the adsorbent may be effected in order to obtain the high degree of purification achieved herein. As a general rule, the purification is conducted under an inert gas atmosphere that is substantially free of oxygen. Nitrogen, helium, argon, neon, and other like inert gases and mixtures thereof may be suitably used. The term "substantially free of oxygen" shall imply an oxygen concentration less than about 1 percent and preferably, less than about 0.1 percent, based on the total volume of gas phase present.

The aforementioned description involves a separate purification step that occurs prior to the metathesis process step, i.e., before the fatty acid or fatty acid ester feedstock contacts the metathesis catalyst; however, one skilled in the art will recognize other engineering realizations of the purification step. For example, the purification step may be designed to occur in situ in the metathesis reactor during the metathesis process itself. Moreover, it is noted that metathesis catalyst poisons generally might poison hydroformylation catalysts and epoxidation catalysts as well. Accordingly, should the metathesis effluent stream be poisoned, or the feedstock be re-poisoned, e.g., by contact with trace amounts or inadvertent leaks of air during storage or conduit, then the purification step may be repeated, as needed, prior to further catalytic processing, e.g., metathesis, hydroformylation, and epoxidation.

As mentioned briefly hereinbefore, the analysis for poisons in the feedstock composition, both before and after purification, can be effected using any suitable analytical tool. For example, the analysis of hydroperoxide concentration may be conducted by means of standard iodide-thiosulfate titrimetric methods, known to those skilled in the art. After the purification process is complete, the feedstock composition is typically converted immediately in the metathesis process or stored under a blanket of inert gas, so as to avoid re-oxidation of the unsaturated fatty acids or fatty acid esters with oxygen.

In addition to the fatty acid or fatty acid ester feedstock composition, the metathesis process of this invention also requires a lower olefin. The term "lower olefin" shall be defined in this instance as a $C_{2-5}$ olefin including, for example, ethylene, propylene, 1-butene, 2-butene, butadiene, pentenes, and mixtures thereof. The lower olefin and feedstock composition may be fed to the metathesis process in any operable amounts. The specific amounts employed can vary depending upon the concentration of unsaturated fatty acids or esters in the feedstock and the specific reactor design. Generally, it is desirable to maintain an amount of lower olefin sufficient to minimize the self-metathesis of the unsaturated fatty acids or esters, that is, metathesis between two molecules of unsaturated fatty acids or ester. Likewise, it is desirable to minimize the self-metathesis of the lower olefin. (In a preferred embodiment wherein the lower olefin is ethylene, self-metathesis is not problematical, because that simply produces ethylene again.) One skilled in the art would know, without undue experimentation, how to choose the relative amounts of lower olefin to feedstock so as to minimize self-metathesis reactions. The following molar ratios are set forth as a guideline, but this invention should not be limited to the ratios disclosed herein. Typically, the molar ratio of lower olefin to total unsaturated fatty acids or fatty acid esters in the feedstock is greater than about 0.1/1.0, preferably, greater than about 0.9/1.0. Typically, the molar ratio of lower olefin to total unsaturated fatty acids or fatty acid esters in the feedstock is less than about 5/1, and preferably, less than about 3/1. In the preferred case wherein the lower olefin is ethylene, the upper limit on the molar ratio of ethylene to total unsaturated fatty acids or fatty acid esters may range up to about 20/1.0. When ethylene is employed, preferably, the molar ratio is less than about 20/1.0, and more preferably, less than about 15/1.0.

Generally, the fatty acid or fatty acid ester feedstock is provided to the metathesis process in a neat liquid phase, that is, without a diluent or solvent. The use of a solvent may increase recycle requirements and costs. Optionally, however, if desired, a solvent can be employed. Non-limiting examples of suitable solvents include aromatic hydrocarbons, such as benzene, toluene, xylenes, and the like; chlorinated aromatic hydrocarbons, preferably chlorinated benzenes, such as chlorobenzene and dichlorobenzene; alkanes, such as pentane, hexane, cyclohexane, and the like; and chlorinated alkanes, such as methylene dichloride and chloroform. If a solvent is used, then any amount can be employed, provided that the metathesis process proceeds as desired. Generally, the concentration of the fatty acid or fatty acid ester feedstock in the solvent is greater than about 0.05 M, preferably, greater than about 0.5 M, typically, less than about the saturation concentration, and preferably, less than about 5.0 M.

Typically, the lower olefin is fed to the reaction as an essentially pure gas or, optionally, diluted with a gaseous diluent. As the gaseous diluent, any essentially inert gas may be used, suitable examples of which include, without limitation, helium, neon, argon, nitrogen, and mixtures thereof. If a gaseous diluent is used, then the concentration of lower olefin in the diluent may suitably range from greater than about 5 mole percent, preferably, greater than about 10 mole percent, to typically less than about 90 mole percent lower olefin, based on the total moles of lower olefin and gaseous diluent. It is beneficial to exclude oxygen from the metathesis process, so as to avoid undesirable reactions of oxygen with the metathesis catalyst and with the unsaturated fatty acids and/or esters.

As a further option, a stabilizing ligand may be added to the metathesis process. The stabilizing ligand may be any molecule or ion that promotes catalyst stability in the metathesis process, as measured, for example, by increased activity and extended catalyst lifetime. Non-limiting examples of stabilizing ligands include tri(alkyl)phosphines, such as tricyclohexylphosphine, tricyclopentylphosphine, and tributylphosphine; tri(aryl)phosphines, such as tri(phenyl)phosphine and tri(methylphenyl)phosphine; alkyldiarylphosphines, such as cyclohexyldiphenylphosphine; dialkylarylphosphines, such as dicyclohexylphenylphosphine; as well as ethers, such as anisole; phosphine oxides, such as triphenylphosphine oxide; and phosphinites, phosphonites, phosphoramidites, pyridines, and combinations thereof. Preferably, the stabilizing ligand is selected from the aforementioned phosphines, and more preferably, is tri(cyclohexyl)phosphine or tri(phenyl)phosphine. The quantity of stabilizing ligand can vary depending upon the specific catalyst employed and its specific ligand components. Typically, the molar ratio of stabilizing ligand to catalyst is greater than about 0.05/1, and preferably, greater than about 0.5/1. Typically, the molar ratio of stabilizing ligand to catalyst is less than about 4.0/1, and preferably, less than about 1.5/1.

The metathesis catalyst may be any catalyst that is capable of facilitating the reaction of an unsaturated fatty acid or unsaturated fatty acid ester with the lower olefin. Many metathesis catalysts are known in the art, representative examples being disclosed in WO 93/20111, U.S. Pat. No. 5,312,940, WO 96/04289; and by J. Kingsbury et al. in *Journal of the American Chemical Society,* 121 (1999), 791-799; as well as in co-pending International Patent Application Serial No. PCT/US 02/05894, filed on Feb. 27, 2002, in the name of Thomas E. Newman, Cynthia Rand, Robert Maughon, Kenneth Burdett, Donald Morrison, and Eric Wasserman; the aforementioned references being incorporated herein by reference. The preferred metathesis catalyst is a ruthenium or osmium metathesis catalyst, more preferably, a ruthenium metathesis catalyst. Non-limiting examples of suitable ruthenium catalysts include dichloro-3,3-diphenylvinylcarbene-bis(tricyclohexylphosphine)ruthenium (II), bis(tricyclohexylphosphine)benzylidene ruthenium dichloride, bis(tricyclohexylphosphine)benzylidene ruthenium dibromide, tricyclohexylphosphine[1,3-bis(2,4,6-trimethylphenyl)-4,5-dihydroimidazol-2-ylidene][benzylidene]ruthenium dichloride, tricyclohexylphosphine[1,3-bis(2,4,6-trimethylphenyl)-4,5-dihydroimidazol-2-ylidene][benzylidene] ruthenium dibromide, and tricyclohexylphosphine[1,3-bis(2,4,6-trimethylphenyl)-4,5-dihydroimidazol-2-ylidene] [benzylidene]ruthenium diiodide. Most preferably, the ruthenium metathesis catalyst is selected from the group consisting of dichloro-3,3-diphenylvinylcarbene-bis(tricyclohexylphosphine)ruthenium (II), bis(tricyclohexylphosphine) benzylidene ruthenium dichloride, and the chelated ruthenium complexes represented by the following formula V:

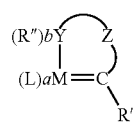

(V)

In formula V, M is Ru; each L is independently selected from neutral and anionic ligands in any combination that balances the bonding and charge requirements of M; a is an integer, preferably from 1 to about 4, which represents the total number of ligands L; R' is selected from hydrogen, straight-chain or branched alkyl, cycloalkyl, aryl, and substituted aryl radicals; Y is an electron donor group of an element from Group 15 or 16 of the Periodic Table, (as referenced by the IUPAC in *Nomenclature of Inorganic Chemistry: Recommendations 1990*, G. J. Leigh, Editor, Blackwell Scientific Publications, 1990); Y being more preferably O, S, N, or P; each R" is independently selected from hydrogen, alkyl, cycloalkyl, aryl, and substituted aryl radicals sufficient to satisfy the valency of Y, preferably such that Y is formally neutral; b is an integer, preferably 0 to about 2, representing the total number of R" radicals; and Z is an organic diradical that is bonded to both Y and the carbene carbon (C) so as to form a bidentate ligand, which ligand in connection with the M atom forms a ring of from about 4 to about 8 atoms. More preferably, each L in formula V is independently selected from the group consisting of halides, most preferably, fluoride, chloride, bromide, and iodide; cyanide, thiocyanate, phosphines of the formula $PR_3$, amines of the formula $NR_3$, water and ethers of the formula $OR_2$, thioethers of the formula $SR_2$, and ligands having the formulas VI and VII hereinafter:

wherein each R in any of the aforementioned formulas is independently selected from the group consisting of hydrogen, alkyl, preferably, $C_{1-15}$ alkyl; cycloalkyl, preferably, $C_{3-8}$ cycloalkyl; aryl, preferably, $C_{6-15}$ aryl, and substituted aryl, preferably $C_{6-15}$ substituted aryl, radicals. Mixtures of any of the aforementioned ligands L may be employed in any given species of formula V. More preferably, R' is selected from the group consisting of hydrogen, $C_{1-15}$ alkyl, $C_{3-8}$ cycloalkyl, and $C_{6-15}$ aryl radicals. More preferably, each R" is independently selected from the group consisting of $C_{1-15}$ alkyl, $C_{3-8}$ cycloalkyl, and $C_{6-15}$ aryl radicals. Preferably, Z is selected from the following diradicals: ethylene (VIII), vinylene (IX), phenylene (X), substituted vinylenes (XI), substituted phenylenes (XII), naphthylene (XIII), substituted naphthylenes (XIV), piperazindiyl (XV), piperidiyl (XVI):

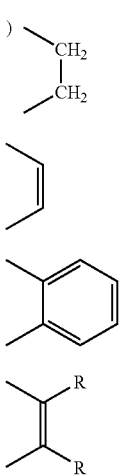

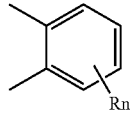

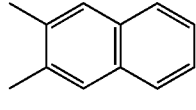

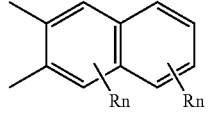

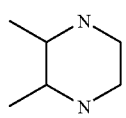

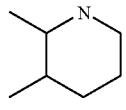

wherein each R may be, as noted above, selected from hydrogen, alkyl, preferably, $C_{1-15}$ alkyl; cycloalkyl, preferably, $C_{3-8}$ cycloalkyl; and aryl, preferably, $C_{6-15}$ aryl, radicals; and wherein each n is an integer from 1 to about 4. The most preferred embodiment of formula V is represented by formula XVII:

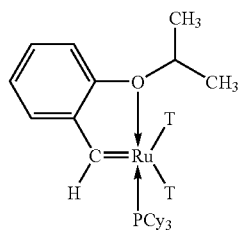

wherein each T is independently selected from Cl and Br, and $PCy_3$ is tricyclohexylphosphine.

Although the metathesis catalyst is preferably a homogeneous catalyst, that is, dissolved in the liquid reaction mixture, the catalyst may be bound to or deposited on any conventional catalyst support known to the skilled artisan, such as silica, alumina, silica-alumina, aluminosilicates, titania, titanosilicates, carbon, reticulated cross-linked polystyrenes, and the like. If a catalyst support is used, the catalyst may be loaded onto the catalyst support in any amount, provided that the metathesis process proceeds to the desired metathesis products. Generally, the catalyst is loaded onto the support in an amount that is greater than about 0.01 weight percent catalytic metal, and preferably, greater than about 0.05 weight percent catalytic metal, based on the total weight of the catalyst plus support. Generally, the catalyst is loaded onto the support in an amount that is less than about 20 weight percent catalytic metal, and preferably, less than about 10 weight percent catalytic metal, based on the total weight of the catalyst and support.

Generally, the reactors and conditions of the metathesis process are conventional, although it should be mentioned that high productivity can be achieved in this process under relatively mild metathesis conditions. Batch reactors, continuous stirred tank reactors, continuous flow fixed bed reactors, slurry reactors, fluidized bed reactors, continuous plug flow reactors, and catalytic distillation reactors may be suitably employed. Typically, the process temperature is greater than about 0° C., preferably, greater than about 15° C., and more preferably, greater than about 25° C. Typically, the process temperature is less than about 80° C., preferably, less than about 50° C., and more preferably, less than about 35° C. Typically, the pressure of lower olefin is greater than about 5 psig (34.5 kPa), preferably, greater than about 10 psig (68.9 kPa), and more preferably, greater than about 45 psig (310 kPa). Typically, the pressure of lower olefin is less than about 500 psig (2,758 kPa), preferably, less than about 250 psig (1,723 kPa), and more preferably, less than about 100 psig (690 kPa).

If the process is conducted in a batch reactor, the ratio of moles of unsaturated fatty acid or fatty acid ester feedstock to moles of metathesis catalyst will typically be greater than about 10:1, preferably, greater than about 50:1, and more preferably, greater than about 100:1. Under such process conditions, the molar ratio of unsaturated fatty acid or fatty acid ester feedstock to metathesis catalyst will be typically less than about 10,000,000:1, preferably, less than about 1,000,000:1, and more preferably, less than about 500,000:1. Generally, the contacting time in a batch reactor is greater than about 5 minutes, and preferably, greater than about 10 minutes. Generally, the contacting time in a batch reactor is less than about 25 hours, preferably, less than about 15 hours, and more preferably, less than about 10 hours.

If the process is conducted in a continuous flow reactor, then the weight hourly space velocity, given in units of grams metathesis feedstock per gram catalyst per hour (h$^{-1}$) determines the relative quantities of unsaturated fatty acid(s) and/or fatty acid ester(s) to catalyst employed, as well as the residence time of the feedstock in the reactor. Accordingly, the weight hourly space velocity of the feedstock is typically greater than about 0.04 g feedstock per g catalyst per hour (h$^{-1}$), and preferably, greater than about 0.1 h$^{-1}$. The weight hourly space velocity of the feedstock is typically less than about 100 h$^{-1}$, and preferably, less than about 20 h$^{-1}$. The flow of lower olefin is typically adjusted to produce the desired ratio of lower olefin to unsaturated fatty acid(s) and/or unsaturated fatty acid ester(s)

When the metathesis process of this invention is conducted as described hereinabove, then the unsaturated fatty acid or fatty acid ester feedstock composition and lower olefin, preferably ethylene, are co-metathesized to form at least two product olefins that are different from the reactant olefins, more specifically, a reduced chain olefin and a reduced chain unsaturated acid or ester. The term "reduced chain" describes a chain length shorter than the chain length in the reactant fatty acid or fatty acid ester. Preferably, the two olefin products comprise a reduced chain α-olefin and a reduced chain α,ω-unsaturated acid or ester. As a more preferred example, the metathesis of feedstocks containing high concentrations of methyloleate with ethylene will yield co-metathesis products of 1-decene and methyl-9-decenoate. The metathesis product mixture comprising the reduced chain olefin, the reduced chain unsaturated acid or ester, metathesis catalyst, and optionally unconverted metathesis feedstock may be separated by conventional methods known to those skilled in the art, including for example, distillation, extraction, precipitation, crystallization, membrane separation, and the like.

The (X-olefin obtained from the metathesis process, preferably, 1-decene, can be used as a monomer in the manufacture of polyolefin polymers.

The reduced chain unsaturated ester obtained from the metathesis is preferably represented by the following formula:

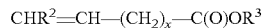

wherein $R^2$ is selected from hydrogen and $C_{1-5}$ monovalent hydrocarbyl radicals, such as, methyl, ethyl, and vinyl radicals, preferably, hydrogen; $R^3$ is a $C_{1-8}$ monovalent alkyl radical, and x is an integer from 3 to about 7. Preferred embodiments include α,ω-unsaturated esters, more preferably, methyl-9-decenoate, ethyl-9-decenoate, propyl-9-decenoate, and butyl-9-decenoate. Most preferably, $R^2$ is hydrogen, $R^3$ is methyl, x is 7, and the α,ω-unsaturated ester is methyl-9-decenoate. Analogously, the most preferred α,ω-unsaturated acid is 9-decenoic acid.

In the metathesis process of this invention, the conversion of unsaturated fatty acid or fatty acid ester can vary widely depending upon the specific feedstock composition, catalyst, and process conditions employed. For the purpose of this invention, "conversion" is defined as the mole percentage of unsaturated fatty acid(s) or unsaturated fatty acid ester(s) that is reacted to products. Typically, the conversion of unsaturated fatty acid(s) or ester(s) is greater than about 10 mole percent, preferably, greater than about 20 mole percent, and more preferably, greater than about 40 mole percent.

The metathesis process of this invention also exhibits an improved catalyst turnover number, that being the moles of unsaturated fatty acid(s) or unsaturated fatty acid ester(s) converted per mole of catalyst. Typically, a turnover number of greater than about 900 is achieved. Preferably, a turnover number of greater than about 1,500, more preferably, greater than about 2,000, and most preferably, greater than about 3,500 is achieved.

In one downstream application, the reduced chain unsaturated acid or ester, preferably, the lower alkyl esters of 9-decenoic acid, can be (trans)esterified with a polyol under (trans)esterification conditions sufficient to prepare the polyester polyolefin of formula (I) hereinabove. One skilled in the art will recognize that it is the reduced chain unsaturated acid that is esterified, whereas it is the reduced chain unsaturated ester that is transesterified. The polyol used in the (trans) esterification may be any polyhydric alcohol capable of such a process, and preferably, is a $C_{2-15}$ polyhydric alcohol. Glycerol is the preferred polyol. The transesterification conditions are similar to the transesterification conditions noted hereinbefore, with the added consideration that effort should be placed in removing the lower alkanol, preferably, methanol, from the reaction mixture. More specifically, the unsaturated ester is typically contacted with the polyol at elevated temperature in the presence of a catalyst, such as n-butyltin hydroxide oxide, with concurrent reactive distillation, or under reduced pressure, to remove the volatile lower alkanol as it is replaced. Typically, on an equivalent basis, a minimum of about 1 equivalent of ester to 1 equivalent of OH groups in the polyol is used. Preferably, an excess of the ester relative to OH is used. As a maximum, preferably, about 2.5 equivalents of ester to 1 equivalent of OH is used. The most preferred range is from about 1.1 to about 1.5 equivalents ester per equivalent OH. The temperature of the transesterification is generally greater than about 100° C. but less than about 250° C. For further description and representative art on transesterification, see JP-A2-01093558 and A. Gros et al., *Journal of the American Oil Chemical Society*, 26 (1949), 704-709, incorporated herein by reference. Similar methods are known in the art for esterifying acids with polyols.

The polyester polyolefin (I) resulting from the (trans)esterification can be epoxidized with an epoxidizing agent, such as a peroxycarboxylic acid, without a catalyst under epoxidation conditions sufficient to prepare a polyester polyepoxide. Alternatively, the epoxidation can be effected using hydrogen peroxide or organic hydroperoxide in the presence of an epoxidation catalyst. Preferred epoxidation agents include hydrogen peroxide, peroxyacetic acid, peroxyformic acid, peroxybenzoic acid, m-chloroperoxybenzoic acid, trifluoroperoxybenzoic acid, t-butyl hydroperoxide, isopentyl hydroperoxide, cyclohexyl hydroperoxide, ethylbenzene hydroperoxide, and cumene hydroperoxide. A variety of organometallic catalysts are known to effect epoxidation including, for example, titanosilicates, such as Ti-Beta, Ti-MCM-41, and Ti-ZSM-5; titanium alkoxides, such as Ti-isopropoxide; tungstates, such as $H_2WO_4$; alumina-supported molybdenum oxide ($MoO_3$); and methyl trioxorhenium. Standard epoxidation conditions include a temperature greater than about ambient, and preferably, greater than about 30° C.; but less than about 130° C., and preferably, less than about 100° C. Pressure is typically ambient, but higher or lower pressures may be used, as needed or desired. Description of epoxidation conditions, including temperature, pressure, relative amounts of reactants, reactor designs, and quantity of catalyst employed, are generally found in the following references incorporated hereby reference: WO 00/18751, ES 2,126,485, WO 01/000605, DE 2,009,047; *Recent Developments in the Synthesis of Fatty Acid Derivatives*, G. Knothe and J. T. P Derksen, Eds., American Oil Chemical Society: Champaign, Ill., 1999, pp. 157-195; and *Handbook of Epoxy Resins*, H. Lee and K. Neville, McGraw-Hill, N.Y., 1982, Chapter 3, pp. 5-12.

The product of the epoxidation process preferably comprises a polyester polyepoxide represented by formula (II) hereinabove. More preferably, the polyester polyepoxide is an α,ω-polyester polyepoxide. Most preferably, the polyester polyepoxide is the triglyceride of 9,10-epoxydecanoic acid. Polyester polyepoxides find utility in epoxy resin applications, including as reactive diluents, flexibilizers, and coatings, and as components of photographic stabilizers.

Alternatively, the reduced chain unsaturated acid or ester, obtained from the metathesis process, can be subjected to hydroformylation with reduction to prepare an α,ω-hydroxy acid, an α,ω-hydroxy ester, and/or an α,ω-diol. In a preferred process, for example, an ester of 9-decenoic acid can be hydroformylated to prepare the corresponding α,ω-formyl ester, e.g., methyl-11-formylundecanoate, which can be reduced to the corresponding α,ω-hydroxy ester, e.g., methyl-11-hydroxyundecanoate, or the corresponding α,ω-diol, e.g., 1,11-undecanediol. Hydroformylation processes generally comprise contacting an olefinic moiety with a mixture of carbon monoxide and hydrogen in the presence of a hydroformylation catalyst, and optionally, in the presence of free organophosphorus ligand, under hydroformylation conditions sufficient to prepare an aldehyde. In the present context, the hydroformylation process will comprise contacting the reduced chain unsaturated acid or ester with carbon monoxide and hydrogen in the presence of a transition metal organophosphorus ligand complex catalyst, and optionally free organophosphorus ligand, under hydroformylation conditions sufficient to prepare a formyl acid or formyl ester, preferably, an α,ω-formyl acid or α,ω-formyl ester. The art fully describes catalysts and conditions for hydroformylation. See, for example, U.S. Pat. No. 6,307,108B1, incorporated herein by reference.

The catalysts useful in the hydroformylation process of this invention include any transition metal organophosphorus ligand complex catalyst that exhibits activity in hydroformylation processes. The suitable metals that make up the metal-organophosphorus ligand complexes includes the Group 8, 9, and 10 metals selected from rhodium (Rh), cobalt (Co), iridium (Ir), ruthenium (Ru), iron (Fe), nickel (Ni), palladium (Pd), platinum (Pt), osmium (Os), and mixtures thereof; with rhodium, cobalt, iridium, and ruthenium being preferred; rhodium, cobalt, and ruthenium being more preferred; and ruthenium being most preferred. Other suitable metals include Group 11 metals selected from copper (Cu), silver (Ag), gold (Au), and mixtures thereof, as well as Group 6 metals selected from chromium (Cr), molybdenum (Mo), tungsten (W), and mixtures thereof. Mixtures of metals from Groups 6, 8, 9, 10, and 11 are also suitable.

The suitable organophosphorus ligands, which make up the free ligand and the ligand complexed in the transition metal-ligand complex catalyst, include, without limitation, organophosphines, e.g., triorganophosphines; and organophosphites, e.g., mono-, di-, and tri-organophosphites and bisphosphites. Other suitable organophosphorus ligands include, for example, organophosphonites, organophosphinites, organophosphorus amides, as well as mixtures of any of the aforementioned ligands. A wide variety of phosphorus ligand species is known in the art, as illustrated, for example, in U.S. Pat. No. 6,307,108B1, incorporated herein by reference.

The reaction conditions for the hydroformylation process encompassed by this invention include any conventional hydroformylation process conditions. For instance, the total gas pressure of hydrogen, carbon monoxide, and olefin starting compound may range from about 1 psia (6.9 kPa) or greater to less than about 10,000 psia (68,950 kPa). Preferably, the total gas pressure is less than about 2,000 psia (13,800 kPa), and more preferably, less than about 1,000 psia (6,850 kPa). More specifically, the carbon monoxide partial pressure of the hydroformylation process of this invention is preferably from greater than about 1 psia (6.9 kPa), and preferably, greater than about 3 psia (20.7 kPa). The carbon monoxide partial pressure is typically less than about 1,000 psia (6,895 kPa), and preferably, less than about 800 psia 5,516 (kPa). The hydrogen partial pressure is typically greater than about 5 psia (34.5 kPa), preferably, greater than about 10 psia (68.9 kPa). The hydrogen partial pressure is typically less than about 500 psia (3,448 kPa), and preferably, less than about 300 psia (2,069 kPa). In general, the $H_2$:CO molar ratio of gaseous hydrogen to gaseous carbon monoxide ranges from about 1:10 to about 10:1. The hydroformylation process is conducted typically at a reaction temperature greater than about −25° C., and preferably, greater than about 50° C. The hydroformylation process is conducted typically at a reaction temperature less than about 150° C., and preferably, less than about 120° C. The exact reaction time will depend upon the particular reactants and catalyst selected; but generally the reaction time is normally within a range of from about 30 minutes to about 200 hours. The hydroformylation process may be conducted in the presence of a solvent, suitable species of which include, without limitation, alkanes, cycloalkanes, aldehydes, ketones, ethers, esters, aromatics, and the like.

As noted hereinbefore, the α,ω-formyl acid or α,ω-formyl ester produced in the hydroformylation process can be hydrogenated in the presence of a hydrogenation agent, typically hydrogen, and typically in the presence of a hydrogenation catalyst to produce the corresponding α,ω-hydroxy acid, α,ω-hydroxy ester, and/or α,ω-diol. The particular process conditions for hydrogenating the α,ω-formyl acid or formyl ester are not narrowly critical, and can be any effective hydrogenation conditions sufficient to produce the desired reduction product. Suitable hydrogenation conditions are referenced by P. N. Rylander, in *Hydrogenation Methods*, Academic Press, New York, 1985, Chapter 5, incorporated herein by reference. Generally, the hydrogenation process is conducted at a temperature greater than about 0° C. and less than about 400° C. for a period of time greater than about 1 minute and less than about 10 hours. The hydrogenation total pressure can vary over a wide range, from greater than about 10 psig (68.9 kPa) to less than about 2,000 psig (13,790 kPa). The hydrogen partial pressure can vary within this range. The hydrogenation step typically requires a hydrogenation catalyst. Such catalysts are known in the art, as noted by P. N. Rylander, Ibid. Preferred catalysts include Raney nickel, Raney cobalt, nickel on silica/alumina, palladium on carbon, platinum on carbon, rhodium on alumina, and the like. The catalyst can be used in conventional amounts, which generally implies a concentration greater than about 5 weight percent, but less than about 50 weight, based on the weight of the formyl acid or formyl ester feed. A solvent may be used, if desired.

The α,ω-hydroxy acid, α,ω-hydroxy ester, and/or α,ω-diol, produced by the hydrogenation step, can be isolated by conventional techniques, such as filtration, crystallization, distillation, extraction, precipitation, membrane separation, or other suitable separation means. Reactive distillation may also be employed in conducting the hydrogenation step. Preferred α,ω-hydroxy esters (ester alcohols) illustrative of those prepared by the process of this invention include methyl-11-hydroxyundecanoate, ethyl-11-hydroxyundecanoate, propyl-11-hydroxyundecanoate, and butyl-11-hydroxyundecanoate, including mixtures thereof; most preferably, methyl-11-hydroxyundecanoate. Likewise, a preferred α,ω-hydroxy acid is 1,11-hydroxyundecanoic acid. A preferred α,ω-diol includes 1,11-dihydroxyundecane.

The α,ω-hydroxy acid or α,ω-hydroxy ester obtained from the hydroformylation process may be (trans)esterified by contact with a polyol under (trans)esterification conditions sufficient to prepare an α,ω-polyester polyol represented by formula (III) hereinabove. A preferred α,ω-polyester polyol is the triglyceride of 11-hydroxyundecanoic acid. Again, the (trans)esterification conditions are similar to those described and cited hereinbefore. The α,ω-polyester polyol finds utility in urethane and epoxy resin applications.

As another alternative, the reduced chain unsaturated acid or ester can be hydroformylated in the presence of a hydroformylation catalyst under hydroformylation conditions sufficient to prepare the corresponding α,ω-formyl acid or α,ω-formyl ester; and thereafter, the α,ω-formyl acid or ester can be reductively aminated under reductive amination conditions sufficient to produce the corresponding α,ω-amino acid, α,ω-amino ester, and/or α,ω-amino alcohol. The hydroformylation step has been described and referenced hereinbefore. The particular reductive amination conditions are not narrowly critical and can be any effective reductive animation conditions sufficient to produce the desired α,ω-amino acid, α,ω-amino ester, or α,ω-amino alcohol. The reactor employed may be a tubular reactor, a stirred-tank reactor, or other conventional reactor suitable for the process. Illustrative reductive amination conditions are described in the art, for example, U.S. Pat. No. 2,777,873, U.S. Pat. No. 4,766,237, U.S. Pat. No. 5,068,398, and U.S. Pat. No. 5,007,934, the disclosures of which are incorporated herein by reference.

More specifically, the reductive amination reaction can be conducted at a temperature greater than about 0° C. and less than about 400° C. for a time ranging from greater than about 1 minute to less than about 10 hours. A wide range of pressure can be used. Typically, the pressure is greater than about 10 psig (68.9 kPa), and preferably, greater than about 100 psig (689.5 kPa), but less than about 4500 psig (31,028 kPa), and preferably, less than about 2000 psig (13,790 kPa). The reductive amination reaction is preferably effected in the liquid or vapor states or mixtures thereof. Ammonia is preferably employed as the aminating agent, and is generally supplied to the process in conventional amounts, preferably excess amounts relative to the α,ω-formyl acid or formyl ester. The ammonia may be fed to the process in a variety of ways, including as a liquid, or as a gas, or in solution in water, e.g., or as an ammonium salt, e.g., urea. Any excess ammonia is preferably separated off after reductive amination is completed. The α,ω-formyl acid or formyl ester is fed to the reductive amination stage in any convenient manner, such as, in solution or as a neat liquid.

The reductive amination step typically is conducted in the presence of a reductive amination catalyst. Suitable catalysts for this step include, for example, Raney nickel, Raney cobalt, nickel on silica/alumina, palladium on carbon, platinum on carbon, rhodium on alumina, and the like, as well as mixtures thereof. The amount of catalyst employed will depend upon the specific reactants and reductive amination conditions employed. The amount should be sufficient to obtain the desired product selectivity and degree of formyl acid or formyl ester conversion. Generally, the amount of catalyst is greater than about 5 weight percent, preferably, greater than about 10 weight percent, and preferably, less than about 20 weight percent, based on the weight of the formyl acid or formyl ester used. The α,ω-amino acid, amino ester, and/or amino alcohol produced by the reductive amination step can be separated by conventional means, including, filtration, distillation, extraction, precipitation, crystallization, membrane separation, and the like. Reactive distillation may also be employed in conducting the reductive amination step.

Illustrative α,ω-amino esters that can be prepared by the process of this invention include methyl 11-aminoundecanoate, ethyl 11-aminoundecanoate, propyl 11-undecanoate, and butyl 11-undecanoate, and the like. The preferred α,ω-amino ester is methyl 11-aminoundecanoate. Likewise, the α,ω-amino acid is 11-aminoundecanoic acid; and the preferred α,ω-amino alcohol is 11-aminoundecanol.

The α,ω-amino acid or α,ω-amino ester obtained from the hydroformylation/reductive amination process may be (trans)esterified by contact with a polyol under (trans)esterification conditions sufficient to prepare an α,ω-polyester polyamine represented by formula (IV) hereinabove. Again, the esterification and transesterification conditions are similar to those described and cited hereinbefore. A preferred polyester polyamine is the triglyceride of 11-aminoundecanoic acid. The α,ω-polyester polyamines find utility in urethane applications and as curing agents in epoxy resins. The latter application is discussed by H. Lee and K. Neville in *Epoxy Resins*, McGraw-Hill, N.Y., 1982, Chapter 7, incorporated herein by reference.

The following examples are provided as illustrations of the process of this invention, but should not be construed as limiting the invention in any manner. In light of the disclosure herein, those of skill in the art will recognize modifications in the reagents, catalyst, and process conditions that fall within the scope of this invention.

General Procedure for Peroxide Analysis

A fatty acid ester derived from a seed oil, specifically methyl oleate, was analyzed for peroxide content in the following manner. In an Erlenmeyer flask (100 ml) having a side-arm, glacial acetic acid (40 ml) and deionized water (10 ml) were combined with stirring using a magnetic stirrer. Through the side-arm, a nitrogen purge was introduced via a syringe into the solution, and stirring was continued for five minutes. To the nitrogen-purged solution, potassium iodide (5 g) was added. Stirring was reinitiated with nitrogen purge for an additional 5 minutes to form a homogeneous solution. To this solution, a sample of methyl oleate was added (5-20 g), and the solution was placed in an oil bath at 110° C. for approximately 5 minutes until near the reflux point. The flask was then removed from the oil bath and returned to the magnetic stirrer where deionized water (40 mL) was added. The resulting yellow-orange solution was then titrated to a colorless endpoint using 0.01 N sodium thiosulfate (aq), from which the peroxide concentration was determined using the following calculation:

[ROOH]=[(X)/(g methyl oleate)]×(N)×1000 wherein [ROOH] is the peroxide concentration in units of milliequivalents peroxide per kilogram fatty acid ester (meq/kg); X is the volume of sodium thiosulfate titration solution in milliliters; and N is the normality of the sodium thiosulfate titration solution in units of meq of thiosulfate per ml titration solution.

Example 1

Example 1 illustrates the purification of a fatty acid ester composition to remove peroxides, and the subsequent metathesis of the purified fatty acid composition with ethylene to yield a reduced chain α-olefin and a reduced chain α,ω-unsaturated ester.

Activated alumina (160 ml, Brockmann I, basic, 150 mesh) was loaded into a glass fritted funnel (350 ml, medium). The funnel was connected to an Erlenmeyer vacuum filtration flask. Methyl oleate (Witco Kemester 205 VEG, 200 mL), containing 305 meq peroxide per kg oleate, was applied to the alumina, and the methyl oleate was allowed to pass through the alumina over the next ten minutes utilizing a vacuum to accelerate the process. Peroxide concentration after treatment was 0.7 meq/kg, as determined by aforementioned iodide-thiosulfate titrimetric method.

Into a clean 2 liter stainless steel Parr reactor equipped with a stirring bar (Mono Mold 3"×¾" facetted football) was added the purified methyl oleate (1400 g, 4.44 moles, 91 percent purity) having the peroxide concentration of 0.7 meq/kg. The reactor was sealed and evacuated for about 20 min at 30 inches of Hg. The evacuated reactor was taken to a cubicle, and a gas feed line was attached to the reactor. The line was purged and vented with nitrogen (300 psig) (2,069 kPa) three times and then purged with ethylene. The reactor was pressurized with ethylene (60 psig) (414 kPa) and stirred for about 10 minutes, after which the stirring was stopped and the reactor vented to ambient pressure. The syringe port valve was immediately opened, and a gas tight syringe containing Grubbs catalyst, bis(tricyclohexylphosphine)-benzylidene ruthenium dichloride, (24.6 mL of 0.04 M Grubbs catalyst dissolved in toluene) was used to deliver the catalyst to the reactor. The port was closed and the ethylene valve was opened. Operating pressure was 60 psig (414 kPa). The large capacity magnetic stirrer was set at full speed for the duration of the 3 h reaction at ambient temperature. Results are set forth in Table 1.

TABLE 1

Effect of peroxide concentration (ROOH) on methyl oleate (MO) conversion and catalyst turnover number (CTN)[1]

| Example | [ROOH] (meq/kg) | MO/Cat Mole Ratio | Rxn. Time (min) | MO Conv (mole %) | CTN (moles MO reacted per mole catalyst) |
|---|---|---|---|---|---|
| CE-1 | 305 | 4500 | 960 | 0% | 0 |
| E-3 | 3.1 | 4500 | 249 | 22% | 990 |
| E-1 | 0.70 | 4500 | 274 | 48% | 2,160 |
| E-2 | 0.30 | 4500 | 249 | 57% | 2,565 |

[1]Process Conditions: Room temperature (~22° C.), 60 psig.

It is seen that a methyl oleate sample containing 0.70 meq peroxide/kg achieved a conversion of 48 mole percent methyl oleate in 274 minutes of reaction time with a turnover number of 2,160.

Example 2

Example 1 was repeated, with the exception that the methyl oleate (Witco) was treated over alumina and found to contain only 0.3 meq peroxides/kg. Metathesis results are shown in Table 1, where it is seen that a turnover number of 2,565 and a conversion of 57 mole percent methyl oleate were achieved in 249 reaction minutes. When Example 2 was compared with Example 1, it was found that the reduction of peroxide concentration from Example 1 to Example 2 led to significant increases in turnover number and conversion at reduced reaction time.

Example 3

Example 1 was repeated, with the exception that a methyl oleate (Witco) was obtained containing only 3.1 meq peroxides/kg, and this methyl oleate was used directly in the metathesis process without treatment over alumina. Metathesis results are shown in Table 1, where it is seen that a turnover number of 990 and a conversion of 22 mole percent methyl oleate were achieved in 249 reaction minutes. When Example 3 was compared with Examples 1 and 2, it was found that as the concentration of peroxide decreased, the turnover number and conversion of methyl oleate increased at comparable or lower reaction times.

Comparative Experiment 1

Example 2 was repeated, with the exception that a methyl oleate (Witco) was obtained having a peroxide concentration of 305 meq/kg, and this methyl oleate was directly used in the metathesis process without treatment over alumina. Results are shown in Table 1. No conversion of methyl oleate was observed up to 960 minutes of reaction time. Accordingly, the turnover number was 0. When Comparative Experiment 1 was compared with Examples 1, 2, and 3, it was concluded that as the concentration of peroxides in the methyl oleate decreased, then catalyst turnover number and oleate conversion increased at reduced reaction times.

Example 4

Example 4 illustrates on a large scale the purification of a fatty acid ester composition and its subsequent metathesis with ethylene to a reduced chain (X-olefin and a reduced chain α,ω-unsaturated ester.

A reactor vessel was assembled comprising a 316 stainless steel Pfaulder reactor (50 gallon) fitted with two beaver tail baffles and agitated by an overhead drive with twin 12" diameter, four inclined bladed, stainless steel impellers, ~20" apart, operating at 337 rpm. A methyl oleate feed (Witco brand methyl oleate) was purified by passing it through a stainless steel column [14 inch diameter (35.6 cm)×8 foot length (2.5 m)]containing alumina (UOP A2 brand alumina, 12×32 mesh). The peroxide concentration of the purified feed was 0.2 meq/kg. The purified feed was fed to the reactor vessel. Using agitation (60-100 rpm), the full reactor (300 lbs, 136.1 kg, 1.1 lb-moles methyl oleate) was sparged with nitrogen gas at atmospheric pressure overnight via a ¼ inch sparge line and vent line. The vent was closed and a vacuum (2.5 psia) (17.2 kPa) was applied for 2 h with the sparge still running. The nitrogen sparge was shut off, and the reactor was evacuated to 1.5 psia (10.3 kPa) for 5 min. The vacuum was shut off; the reactor was filled with ethylene and allowed to reach ethylene saturation at 75 psia (517 kPa) under full agitation. Ethylene was fed on demand during the metathesis reaction to maintain a reaction pressure of 74-75 psia (510-517 kPa) ethylene.

Three catalyst shot tanks, each containing Grubbs catalyst [bis(tricyclohexylphosphine)benzylidene ruthenium (IV) dichloride] in anhydrous toluene (Aldrich, 1 liter, 300 ppm by weight water), were prepared in a dry box, and one at a time attached to the reactor catalyst feed port. The secured shot tank was pressurized with nitrogen (80 psia) (552 kPa), and a feed valve was opened to allow the catalyst solution to be blown into the reactor. The feed valve was closed; the empty cylinder removed, and the next full cylinder secured in place. This procedure was repeated for each of the three shot cylinders. About 35 minutes of reaction time elapsed between catalyst additions. The methyl oleate:total catalyst mole ratio was 4,500:1.

The reaction was agitated for 4 h after the first shot of catalyst with the temperature being maintained at 25-26° C. via jacket cooling. At the end of the 4 h reaction time, the product mixture was pumped from the reactor to a tank inerted with nitrogen at atmospheric pressure. A gas chromatographic sample taken of the product mixture indicated a methyl oleate conversion of 39.5 mole percent with a 95 percent selectivity to each of 1-decene and methyl-9-decenoate. The catalyst turnover number was found to be 1,689.

Example 5

Example 5 illustrates the purification of a fatty acid ester composition and its subsequent metathesis with ethylene. A metathesis of methyl oleate was conducted in accordance with the procedures of Example 1, with the following differences: (a) The methyl oleate feed comprised 99 weight percent oleic acid esters (Aldrich), instead of 85 weight percent oleic acid esters. (b) The peroxide concentration of the purified feed was 0.40 meq/kg. (c) The methyl oleate to catalyst mole ratio was 18,000:1. Under process conditions similar to Example 1, a catalyst turnover number of 8,100 was observed.

Comparative Experiment 2

The metathesis of methyl oleate (Aldrich) was conducted in accordance with the procedures of Example 5, with the following differences. (a) The peroxide concentration was 26.3 meq/kg. (b) The methyl oleate to catalyst mole ratio was 4,500:1. Under process conditions similar to Example 5, no catalyst activity was observed. When Example 5 was compared with Comparative Experiment 2, it was found that the reduction of peroxide concentration in the methyl oleate feed from 26.3 meq/kg to 0.4 meq/kg produced active catalyst of higher turnover number (8,100) at higher oleate to catalyst mole ratio (18,001). In contrast, the comparative process having a higher peroxide concentration showed no activity, even though substantially more catalyst was present (oleate to catalyst 4,500:1). This comparative experiment also illustrates the sensitivity of the metathesis catalyst, herein bis (tricyclohexylphosphine)benzylidene ruthenium dichloride, to 26 meq peroxides/kg. This example may be compared with later Example 9, which employs a different metathesis catalyst {tricyclohexylphosphine[1,3-bis(2,4,6-trimethylphenyl)-4,5-dihydroimidazol-2-ylidene][benzylidene]ruthenium dichloride} that exhibits activity at about 100 meq peroxides/kg feedstock.

Example 6

Example 6 illustrates the hydroformylation/reduction of an α,ω-unsaturated ester, specifically, methyl-9-decenoate, to yield a α,ω-hydroxy ester, specifically, methyl-11-hydroxyundecanoate. Methyl-9-decenoate was obtained by the procedures described in any of Examples 1-5 hereinabove.

A hydroformylation reaction was carried out in a Parr reactor (300 mL capacity) equipped with a mechanical stirrer, gas inlet tube, heating jacket, pressure transducer and thermocouple. The reactor was charged with methyl-9-decenoate (100 g, 0.54 mol), acetylacetonate(dicarbonyl)-rhodium (II) [Rh(CO)$_2$ acac] (32 mg, 0.12 mmol), and 2,7-di-tert-butyl-9,9-dimethyl-4,5-bis(diphenylphosphino)xanthene (342 mg, 0.49 mmol) under nitrogen, and then the reactor was sealed. The reactor was connected to a feed line for delivering synthesis gas (CO/H$_2$, 1:1). The system was flushed with synthesis gas twice and then pressurized to 450 psi (3,103 kPa). The reactor was heated to 85° C. for 16 h while maintaining 450 psi (3,103 kPa) of syn gas pressure. After 16 h, the temperature was raised to 100° C. and heated for an additional 4 h. The reactor was cooled to ambient temperature and the unreacted gas was vented. After flushing the reactor with nitrogen to remove the last traces of syn gas, dioxane (50 ml) and 1 g of 5% Pt/SiO$_2$ were introduced to the reactor. The system was flushed with hydrogen twice and pressurized to 500 psi (3,448 kPa) with hydrogen. The mixture was then heated to 150° C. for 20 h maintaining 500 psi (3,448 kPa) of hydrogen pressure. After cooling, the contents were filtered to remove the solid catalyst, and the solvent was removed by rotary evaporation. The resulting liquid was subjected to distillation under reduced pressure. The fraction boiling at 140-150° C. (1.5 mm pressure) was collected and dissolved in 1200 mL of hexanes. The solution was then allowed to crystallize in a freezer for 18 h. White crystals were collected by cold filtration and washed once with cold hexanes. Drying under reduced pressure yielded methyl 11-hydroxyundecanoate as white solid (77 g; 65% overall yield). Conversion of methyl 11-hydroxyundecanoate via transesterification with a polyol, such as glycerol, to the corresponding polyester polyol, such as the triglyceride of 11-hydroxyundecanoic acid, can be effected by transesterification methods known in the art.

Example 7

Example 7 illustrates the preparation of the triglyceride ester of 9,10-epoxydecanoic acid. Glycerin (73.65 g, 2.4 equiv.), methyl 9-decenoate (540.1 g, 2.93 equiv.) and sodium methoxide (25% in methanol, 3.89 g, 0.0182 equiv.) were added to a four-neck, 500-mL round bottom flask. The flask was fitted with a side arm condenser with collection flask followed by a cold trap and a drying tower. The mixture was heated to 200° C. under nitrogen purge with agitation. The methanol distillate was collected. The reaction was completed after a total heating period of about 22 h as determined by gas chromatography. The reaction mixture was cooled to room temperature. The base catalyst was neutralized by the addition of glacial acetic acid (0.84 g; 0.014 equiv.). The mixture was then filtered and water washed until the water layer had a pH of approximately 7-8. The excess methyl 9-decenoate was removed by vacuum distillation. The final distillation conditions were 200° C. and 1 mm Hg. The final product, the triglyceride of 9-decenoic acid, had an iodine number of 127 (Theory=139). (Iodine number is a measure of the unsaturation present in the sample).

The triglyceride of 9-decenoic acid (100 g, 0.493), prepared hereinabove, was placed in a three-neck round bottom flask equipped with a magnetic stir bar, addition funnel, thermocouple, and vacuum reflux condenser cooled with 0° C. circulated glycol. Peracetic acid (23% in ethyl acetate; 200 g, 0.591 equiv.) was added to the addition funnel. The reaction flask was heated to 50° C., then peracetic acid addition was begun. When sufficient peracetic acid solution was added, a slight vacuum was applied through the top of the condenser to maintain reflux at 55° C. The peracetic acid addition was completed in 40 minutes. The mixture was heated at 55° C. for an additional 4 hours then cooled to room temperature. The product was isolated by removing most of the volatile components on a rotary evaporator at reduced pressure (approximately 25° C. with a slight nitrogen sparge). The final stripping conditions were 80° C. at about 0.1 mm Hg for about 20 minutes. The final product, identified as the triglyceride of 9,10-epoxydecanoic acid, had an epoxide equivalent weight of approximately 227 g/equiv. (Theoretical: 199 g/equiv.)

Example 8

Example 8 illustrates the metathesis of a purified feedstock of methyl oleate with ethylene, as a function of the molar ratio of methyl oleate to catalyst (MO/Cat). The metathesis was conducted in accordance with the procedures of Example 1, with the following differences: (1) The methyl oleate feed comprised 99 weight percent oleic acid esters (Aldrich), instead of 85 weight percent oleic acid esters. (b) The peroxide concentration of the purified feed was less than 0.2 meq/kg (detection limit). (c) The methyl oleate to catalyst mole ratio was varied from 4,633:1 to 103,000:1. The process was run under process conditions similar to Example 1 with the results shown in Table 2.

TABLE 2

Catalyst turnover number (CTN)
as a Function of Methyl Oleate to Catalyst
Mole Ratio (MO/Cat)[1]

| MO/Cat Mole Ratio | CTN |
|---|---|
| 4,633 | 3,125 |
| 7,123 | 4,548 |
| 17,100 | 10,700 |
| 51,593 | 12,833 |
| 103,000 | 16,069 |

[1]Process Conditions: Room temperature (~22° C.), 60 psig.

From Table 2 it was seen that the catalyst turnover number increased with increasing molar ratio of methyl oleate to catalyst.

Example 9

Example 9 illustrates the impact of hydroperoxide concentration on a metathesis catalyst consisting of tricyclohexylphosphine[1,3-bis(2,4,6-trimethylphenyl)-4,5-dihydroimidazol-2-ylidene][benzylidene]ruthenium dichloride. The metathesis of methyl oleate was conducted in accordance with the procedures of Example 1, with the following differences: (a) The methyl oleate feed comprised 99 weight percent oleic acid esters (Aldrich), instead of 85 weight percent oleic acid esters. (b) The peroxide concentration of the purified feed was less than 0.2 meq/kg (detection limit). (c) The methyl oleate to catalyst mole ratio (MO/Cat) was maintained at 4,500:1. (d) Cumene hydroperoxide was added to the methyl oleate at controlled concentrations, and the impact on catalyst turnover number was evaluated. The metathesis was conducted under process conditions similar to Example 1, with the results shown in Table 3.

TABLE 3

Catalyst turnover number (CTN)
as a Function of Peroxide Concentration[1]

| meq ROOH per kg | CTN |
|---|---|
| <0.2 | 450 |
| 26 | 330 |
| 52 | 243 |
| 104 | 176 |

[1]Process Conditions: Room temperature (~22° C.), 60 psig.

Thus, the catalyst consisting of tricyclohexyl-phosphine[1,3-bis(2,4,6-trimethylphenyl)-4,5-dihydroimidazol-2-ylidene][benzylidene]ruthenium dichloride exhibited activity (CTN) at 104 meq/kg peroxide concentration; however, catalyst activity improved significantly as the peroxide concentration decreased.

The invention claimed is:

1. A fatty acid or fatty acid ester composition comprising one or more unsaturated fatty acids or one or more unsaturated fatty acid esters, characterized as comprising less than 1.5 milliequivalents of metathesis catalyst poison(s) per kilogram (meq/kg) of fatty acid or fatty acid ester composition, wherein the metathesis catalyst poison comprises one or more organic hydroperoxides; the feedstock composition being prepared by hydrolyzing a seed oil with water to obtain one or more unsaturated fatty acids or transesterifying a seed oil with a $C_{1-8}$ alkanol to prepare one or more unsaturated fatty acid esters of the $C_{1-8}$ alkanol, and thereafter contacting the one or more unsaturated fatty acids or one or more unsaturated fatty acid esters with an adsorbent to remove the metathesis catalyst poison(s) to a concentration of less than 1.5 meq/kg.

2. The fatty acid or fatty acid ester composition of claim 1 comprising less than about 1.0 meq/kg of metathesis catalyst poison(s).

3. The fatty acid or fatty acid ester composition of claim 1 comprising greater than about 70 weight percent unsaturated fatty acid(s) and/or unsaturated fatty acid ester(s).

4. The fatty acid or fatty acid ester composition of claim 3 wherein the unsaturated fatty acid is oleic acid, or the unsaturated fatty acid ester is an ester of oleic acid.

5. The fatty acid ester composition of claim 4 wherein the unsaturated fatty acid ester is the methyl ester of oleic acid.

6. The fatty acid or fatty acid ester composition of claim 1 wherein the adsorbent is selected from the group consisting of aluminas, silicas, activated carbons, clays, magnesias, aluminosilicates, molecular sieves, titanosilicates, and mixtures thereof.

7. An olefin metathesis process comprising contacting a feedstock composition derived from a seed oil and comprising one or more unsaturated fatty acids or one or more unsaturated fatty acid esters with a lower olefin in the presence of a metathesis catalyst under metathesis process conditions sufficient to prepare a reduced chain olefin and a reduced chain unsaturated acid or unsaturated ester, the feedstock composition characterized as comprising less than 10 milliequivalents of metathesis catalyst poison(s) per kilogram (meq/kg) of feedstock composition wherein the metathesis catalyst poison comprises one or more organic hydroperoxides, and the feedstock composition is prepared by hydrolyzing a seed oil with water to obtain one or more unsaturated fatty acids or transesterifying a seed oil with a $C_{1-8}$ alkanol to prepare one or more unsaturated fatty acid esters of the $C_{1-8}$ alkanol, and thereafter contacting the one or more unsaturated fatty acids or one or more unsaturated fatty acid esters with an adsorbent to remove the metathesis catalyst poison(s) to a concentration of less than 10 meq/kg.

8. The process of claim 7 wherein the feedstock composition comprises less than about 3.0 meq organic hydroperoxides per kg feedstock composition.

9. The process of claim 8 wherein the feedstock composition comprises less than about 1.0 meq organic hydroperoxides per kg feedstock composition.

10. The process of claim 7 wherein the feedstock composition comprises greater than about 70 weight percent unsaturated fatty acid(s) or unsaturated fatty acid ester(s).

11. The process of claim 10 wherein the feedstock composition comprises greater than about 70 weight percent oleic acid or oleic acid ester(s).

12. The process of claim 7 wherein the metathesis is conducted in the presence of a transition metal organophosphorus complex catalyst.

13. The process of claim 12 wherein the metathesis catalyst is selected from the group consisting of dichloro-3,3-diphenylvinylcarbene-bis(tricyclohexylphosphine)ruthenium (II), bis(tricyclohexylphosphine)benzylidene ruthenium dichloride, bis(tricyclohexylphosphine)benzylidene ruthenium dibromide, tricyclohexylphosphine[1,3-bis(2,4,6-trimethylphenyl)-4,5-dihydroimidazol-2-ylidene][benzylidene]ruthenium dichloride, tricyclohexylphosphine[1,3-bis(2,4,6-trimethylphenyl)-4,5-dihydroimidazol-2-ylidene][benzylidene]ruthenium dibromide, tricyclohexylphosphine[1,3-bis(2,4,6-trimethylphenyl)-4,5-dihydroimidazol-2-ylidene][benzylidene]ruthenium diiodide, and the chelated ruthenium complexes represented by the following formula:

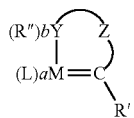

wherein M is Ru; each L is independently selected from neutral and anionic ligands in any combination that balances the bonding and charge requirements of M; a is an integer from 1 to about 4; R' is selected from hydrogen, straight-chain or branched alkyl, cycloalkyl, aryl, and substituted aryl radicals; Y is an electron donor group of an element from Group 15 or 16 of the Periodic Table; each R" is independently selected from hydrogen, alkyl, cycloalkyl, aryl, and substituted aryl radicals sufficient to satisfy the valency of Y; b is an integer from 0 to about 2; and Z is an organic diradical that is bonded to both Y and the carbene carbon (C) so as to form a bidentate ligand, which ligand in connection with the M atom forms a ring of from about 4 to about 8 atoms.

14. The process of claim 7 wherein the lower olefin is selected from $C_{2-5}$ olefins.

15. The process of claim 7 wherein the reduced chain olefin is a reduced chain α-olefin, and the reduced chain unsaturated ester is a reduced chain α,ω-unsaturated ester.

16. The process of claim 15 wherein the reduced chain α-olefin is 1-decene, and the reduced chain α,ω-unsaturated ester is methyl 9-decenoate.

17. A process of preparing a polyester polyepoxide comprising (1) contacting a feedstock composition derived from a seed oil comprising one or more unsaturated fatty acids or one or more unsaturated fatty acid esters with a lower olefin in the presence of an olefin metathesis catalyst under metathesis process conditions sufficient to prepare a reduced chain unsaturated acid or reduced chain unsaturated ester; (2) (trans)esterifying the reduced chain unsaturated acid or ester with a polyol under (trans)esterification conditions sufficient to prepare a polyester polyolefin; and (3) epoxidizing the polyester polyolefin with an epoxidizing agent, optionally, in the presence of an epoxidation catalyst, under epoxidation conditions sufficient to prepare a polyester polyepoxide; the feedstock composition of step (1) comprising less than 10 milliequivalents of metathesis catalyst poison(s) per kilo ram (meq/kg) of feedstock composition, wherein the metathesis catalyst poison comprises one or more organic hydroperoxides, and the feedstock composition is prepared by hydrolyzing a seed oil with water to obtain one or more unsaturated fatty acids or transesterifying a seed oil with a $C_{1-8}$ alkanol to prepare one or more unsaturated fatty acid esters of the $C_{1-8}$ alkanol, and thereafter contacting the one or more unsaturated fatty acids or one or more unsaturated fatty acid esters with an adsorbent to remove the metathesis catalyst poison(s) to a concentration of less than 10 meq/kg.

18. The process of claim 17 wherein the lower olefin is ethylene.

19. The process of claim 17 wherein the olefin product is an α-olefin, and the unsaturated ester is an α,ω-unsaturated ester.

20. A process of preparing a reduced chain α,ω-hydroxy acid, α,ω-hydroxy ester, and/or α,ω-diol comprising (1) contacting a feedstock composition comprising one or more unsaturated fatty acids or one or more unsaturated fatty acid esters with a lower olefin in the presence of an olefin metathesis catalyst under process conditions sufficient to prepare a reduced chain unsaturated acid or ester; and (2) subjecting the reduced chain unsaturated acid or ester to hydroformylation with reduction in the presence of a hydroformylation/reduction catalyst under hydroformylation/reduction conditions sufficient to produce an α,ω-hydroxy acid, an α,ω-hydroxy ester, and/or an α,ω-diol; the feedstock composition of step (1) comprising less than 10 milliequivalents of metathesis catalyst poison(s) per kilogram (meq/kg) of feedstock composition, wherein the metathesis catalyst poison comprises one or more organic hydroperoxides, and the feedstock composition is prepared by hydrolyzing a seed oil with water to obtain one or more unsaturated fatty acids or transesterifying a seed oil with a $C_{1-8}$ alkanol to prepare one or more unsaturated fatty acid esters of the $C_{1-8}$ alkanol, and thereafter contacting the one or more unsaturated fatty acids or the one or more unsaturated fatty acid esters with an adsorbent to remove the metathesis catalyst poison(s) to a concentration of less than 10 meq/kg.

21. The process of claim 20 wherein the lower olefin is ethylene.

22. The process of claim 20 wherein the α,ω-hydroxy acid or α,ω-hydroxy ester is (trans)esterified by contact with a polyol under (trans)esterification conditions sufficient to prepare an α,ω-polyester polyol.

23. A process of preparing a reduced chain α,ω-amino acid, α,ω-amino ester, and/or α,ω-amino alcohol comprising (1) contacting a feedstock composition comprising one or more unsaturated fatty acids or one or more unsaturated fatty acid esters with a lower olefin in the presence of an olefin metathesis catalyst under process conditions sufficient to prepare a reduced chain unsaturated acid or ester; and thereafter (2) subjecting the reduced chain unsaturated acid or ester to hydroformylation with reductive amination in the presence of a hydroformylation catalyst under hydroformylation/reductive amination conditions sufficient to produce an α,ω-amino acid, an α,ω-amino ester, and/or an α,ω-amino alcohol; the feedstock composition of step (1) comprising less than 10 milliequivalents of metathesis catalyst poison(s) per kilogram (meq/kg) of feedstock composition, wherein the metathesis catalyst poison comprises one or more organic hydroperoxides, and the feedstock composition is prepared by hydrolyzing a seed oil with water to obtain one or more unsaturated fatty acids or transesterifying a seed oil with a $C_{1-8}$ alkanol to prepare one or more unsaturated fatty acid esters of the $C_{1-8}$ alkanol, and thereafter contacting the one or more unsaturated fatty acids or the one or more unsaturated fatty acid esters with an adsorbent to remove the metathesis catalyst poison(s) to a concentration of less than 10 meq/kg.

24. The process of claim 23 wherein the lower olefin is ethylene.

25. The process of claim 23 wherein the α,ω-amino acid or α,ω-amino ester is (trans)esterified by contacting the α,ω-amino acid or ester with a polyol under (trans)esterification conditions sufficient to prepare an α,ω-polyester polyamine.

* * * * *

UNITED STATES PATENT AND TRADEMARK OFFICE
CERTIFICATE OF CORRECTION

| | |
|---|---|
| PATENT NO. | : 7,745,652 B2 |
| APPLICATION NO. | : 12/328868 |
| DATED | : June 29, 2010 |
| INVENTOR(S) | : Zenon Lysenko et al. |

It is certified that error appears in the above-identified patent and that said Letters Patent is hereby corrected as shown below:

In the specification, page one is amended by adding a paragraph before the Cross-Reference to Related Applications paragraph on page one, line 4 to read as follows:

This invention was made with U.S. Government support under contract DE-FC36-01ID14213 awarded by the Department of Energy. The U.S. Government has certain rights in this invention.

Signed and Sealed this
Twenty-seventh Day of November, 2012

David J. Kappos
*Director of the United States Patent and Trademark Office*